US012245926B2

(12) United States Patent
Tomita et al.

(10) Patent No.: US 12,245,926 B2
(45) Date of Patent: Mar. 11, 2025

(54) ABSORBENT ARTICLE

(71) Applicant: KAO CORPORATION, Tokyo (JP)

(72) Inventors: Mina Tomita, Utsunomiya (JP); Yuko Fukuda, Mashiko-machi (JP)

(73) Assignee: KAO CORPORATION, Tokyo (JP)

( * ) Notice: Subject to any disclaimer, the term of this patent is extended or adjusted under 35 U.S.C. 154(b) by 1088 days.

(21) Appl. No.: 17/059,371

(22) PCT Filed: May 27, 2019

(86) PCT No.: PCT/JP2019/020887
§ 371 (c)(1),
(2) Date: Nov. 27, 2020

(87) PCT Pub. No.: WO2019/230646
PCT Pub. Date: Dec. 5, 2019

(65) Prior Publication Data
US 2021/0236351 A1    Aug. 5, 2021

(30) Foreign Application Priority Data

May 29, 2018 (JP) ................................ 2018-102882

(51) Int. Cl.
*A61F 13/511* (2006.01)
*A61F 13/49* (2006.01)
(Continued)

(52) U.S. Cl.
CPC ........ *A61F 13/51104* (2013.01); *A61F 13/49* (2013.01); *A61H 19/30* (2013.01);
(Continued)

(58) Field of Classification Search
CPC .... A61B 5/14546; A61F 13/49; A61F 13/511; A61F 13/51104; A61F 2013/15284;
(Continued)

(56) References Cited

U.S. PATENT DOCUMENTS 2,622,051 A * 12/1952 Hermanson ........... B31F 1/2895
  428/48
5,702,376 A * 12/1997 Glaug ..................... A61F 13/42
  604/291
(Continued)

FOREIGN PATENT DOCUMENTS

AU    2013358099 A1   7/2015
CN    101219078 A     7/2008
(Continued)

OTHER PUBLICATIONS

Extended European Search Report for European Application No. 19811555.2, dated Feb. 22, 2022.
(Continued)

*Primary Examiner* — Catharine L Anderson
*Assistant Examiner* — Jihad Dakkak
(74) *Attorney, Agent, or Firm* — Birch, Stewart, Kolasch & Birch, LLP

(57) ABSTRACT

Disclosed is an absorbent article including a projecting-and-depressed sheet (10) as a constituent member, the absorbent article having a longitudinal direction and a width direction orthogonal to the longitudinal direction. The projecting-and-depressed sheet (10) has a plurality of depressions (3) and projections (4) on a skin-facing surface to be brought into contact with the wearer's skin. In a given direction, a movable range of an apex (40a) of the projection (4) of the projecting-and-depressed sheet (10) is 30% or greater to the length (L2) of a bottom portion of the projection (4). On the skin-facing surface of the projecting-and-depressed sheet (10), the mean friction coefficient MIU in the longitudinal direction (X) is 0.3 or less, and a difference in friction coefficient between a forward path and a return path when moved back and forth along the longitudinal direction (X) is less than 0.1. The projecting-and-depressed sheet (10) has a (Continued)

work of compression of 2.0 mN·cm/cm² or greater and a compression recovery rate of 40% or greater.

14 Claims, 8 Drawing Sheets

(51) Int. Cl.
   *A61H 19/00*     (2006.01)
   *A61M 21/02*     (2006.01)
   *A61B 5/145*     (2006.01)
   *A61F 13/15*     (2006.01)
   *A61F 13/513*    (2006.01)
   *A61M 21/00*     (2006.01)

(52) U.S. Cl.
   CPC ......... *A61M 21/02* (2013.01); *A61B 5/14546* (2013.01); *A61F 2013/15284* (2013.01); *A61F 2013/51178* (2013.01); *A61F 2013/51182* (2013.01); *A61F 2013/51316* (2013.01); *A61F 2013/51338* (2013.01); *A61M 2021/0022* (2013.01)

(58) Field of Classification Search
   CPC .. A61F 2013/51178; A61F 2013/51182; A61F 2013/51316; A61F 2013/51338; A61H 19/30; A61M 2021/0022; A61M 21/02
   See application file for complete search history.

(56) References Cited

U.S. PATENT DOCUMENTS

| | | | | |
|---|---|---|---|---|
| 6,432,094 | B1* | 8/2002 | Fujioka | A61F 13/494 |
| | | | | 604/385.101 |
| 8,784,972 | B2 | 7/2014 | Sato et al. | |
| 9,283,125 | B2* | 3/2016 | Otsubo | A61F 13/51464 |
| 2001/0014796 | A1* | 8/2001 | Mizutani | A61F 13/51121 |
| | | | | 604/383 |
| 2002/0058128 | A1* | 5/2002 | Toyoshima | A61F 13/51108 |
| | | | | 428/182 |
| 2003/0143376 | A1* | 7/2003 | Toyoshima | A61F 13/5116 |
| | | | | 428/196 |
| 2004/0140047 | A1 | 7/2004 | Sato et al. | |
| 2010/0249740 | A1* | 9/2010 | Miyamoto | D04H 1/559 |
| | | | | 428/166 |
| 2012/0165774 | A1 | 6/2012 | Otsubo et al. | |
| 2017/0065460 | A1* | 3/2017 | Rosati | A61F 13/539 |
| 2017/0121873 | A1* | 5/2017 | Kimura | A61F 13/51104 |
| 2017/0181901 | A1 | 6/2017 | Ehrnsperger et al. | |
| 2017/0318401 | A1 | 11/2017 | Ludher et al. | |
| 2022/0378631 | A1* | 12/2022 | Garcia | B32B 5/022 |

FOREIGN PATENT DOCUMENTS

| | | | |
|---|---|---|---|
| CN | 107708835 A | 2/2018 | |
| GB | 2559705 A | 8/2018 | |
| JP | 2002-16583 | 6/2002 | |
| JP | 2003-220660 A | 8/2003 | |
| JP | 2004-174234 A | 6/2004 | |
| JP | 2007-181662 A | 7/2007 | |
| JP | 2014-79291 A | 5/2014 | |
| JP | 2014-83228 A | 5/2014 | |
| JP | 6131273 B2 | 5/2017 | |
| JP | 2017-186728 A | 10/2017 | |
| JP | 2019132822 A * | 8/2019 | |
| RU | 2 466 872 C2 | 11/2012 | |
| WO | WO-2015146717 A1 * | 10/2015 | ............. A61F 13/15 |
| WO | WO-2017014213 A1 * | 1/2017 | ............. A61F 13/511 |
| WO | WO 2017/086076 A1 | 5/2017 | |

OTHER PUBLICATIONS

"How to interact with the happy hormone oxytocin" [online], Oct. 28, 2016, Total 4 pages. <URL:https://www.cosmopolitan.com/jp/beauty-fashion/health/news/a3374/oxytocin/>.

Andari et al., "Promoting social behavior with oxytocin in high-functioning autism spectrum disorders", Proc. Natl. Acad. Sci. USA, 2010, vol. 107, No. 9, pp. 4389-4394.

Hikima et al., "Study for Physiological psychology of skin care behavior", Program and Abstracts of the 35th Annual Meeting of the Japanese Society for Physiological Psychology and Psychophysiology, 2017, vol. 59, pp. 1-3.

International Search Report (PCT/ISA/210) issued in PCT/JP2019/020887 mailed on Aug. 27, 2019.

Löken et al., "Coding of pleasant touch by unmyelinated afferents in humans", Nature Neuroscience, 2009, vol. 12, pp. 547-548.

Morhenn et al., "Massage Increases Oxytocin and Reduces Adrenocorticotropin Hormone in Humans", Altern. Ther. Health. Med., 2012, vol. 18, No. 6, pp. 11-18.

Uvnas-Moberg et al., "Self-soothing behaviors with particular reference to oxytocin release induced by non-noxious sensory stimulation," Frontiers in Psychology, vol. 5, No. 1529, Jan. 2015, pp. 1-16.

* cited by examiner

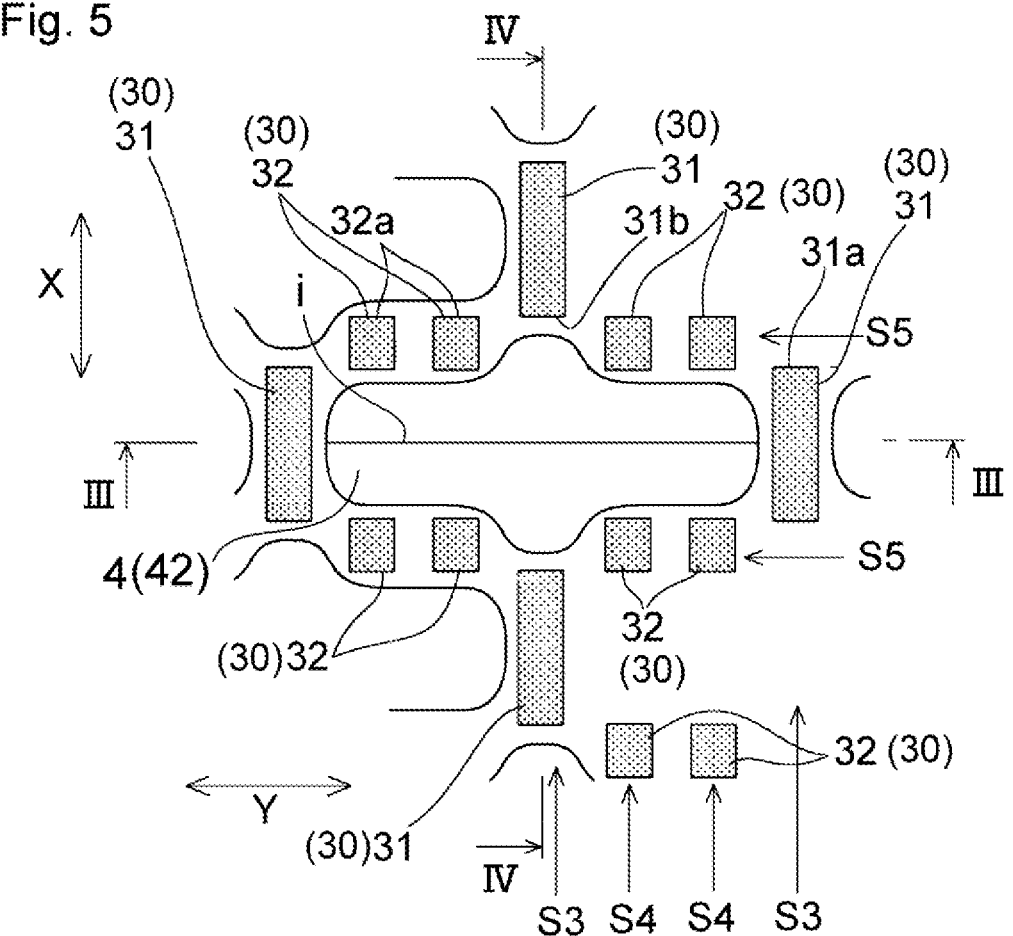

ABSORBENT ARTICLE

TECHNICAL FIELD

The present invention relates to absorbent articles, such as disposable diapers, sanitary napkins, and incontinence pads.

BACKGROUND ART

Various studies are being made regarding sheets that come into contact with the wearer's skin in absorbent articles, such as disposable diapers, with the aim of improving texture to the touch, such as softness. For example, Patent Literature 1 discloses an absorbent article including a nonwoven fabric laminate made by layering two or more layers of: a spunbond nonwoven fabric layer wherein a web is formed by using a material including a softening agent; and a meltblown nonwoven fabric layer, wherein the nonwoven fabric laminate is arranged such that the spunbond nonwoven fabric layer is located on the outer surface of the absorbent article.

There are also known absorbent articles including a sheet wherein a three-dimensional shape is formed on the surface that comes into contact with the wearer's skin. Applicant has previously proposed, from the viewpoint of obtaining liquid leakage preventability, an absorbent article including a topsheet wherein: an upper layer and a lower layer are partially joined together by joined portions; the upper layer protrudes in sections other than the joined portions, to thereby form projections having a hollow interior; there are a plurality of rows, each including a plurality of the projections and joined portions lined up alternately in one direction; and, when focusing on a discretionary one of the projections in one row, there are no projections in positions adjacent to that one projection in rows to the left and right of that one row.

CITATION LIST

Patent Literature

Patent Literature 1: JP 2003-220660A
Patent Literature 2: JP 2004-174234A

Non-Patent Literature

Non-Patent Literature 1: Loken et al., Nature Neuroscience, Vol. 12, pp. 547-548, 2009.
Non-Patent Literature 2: Rie Hikima et al., Program and Abstracts of the 35th Annual Meeting of the Japanese Society for Physiological Psychology and Psychophysiology, 59, 2017.
Non-Patent Literature 3: Morhenn et al., Altern. Ther. Health. Med., 18, 11-18, 2012.
Non-Patent Literature 4: Andari E. et al., Proc. Natl. Acad. Sci. USA, 107(9): 4389-94, 2010.

SUMMARY OF INVENTION

The present invention relates to an absorbent article including a projecting-and-depressed sheet as a constituent member, the absorbent article having a longitudinal direction that corresponds to a front-rear direction of a wearer and a width direction that is orthogonal to the longitudinal direction. The projecting-and-depressed sheet has a plurality of depressions and projections on a skin-facing surface to be brought into contact with the wearer's skin. In a given direction, a movable range of an apex of the projection of the projecting-and-depressed sheet is 30% or greater to a length of a bottom portion of the projection. On the skin-facing surface of the projecting-and-depressed sheet, a mean friction coefficient MIU in the given direction is 0.3 or less, and a difference in friction coefficient between a forward path and a return path when moved back and forth along the given direction is less than 0.1. The projecting-and-depressed sheet has a work of compression of 2.0 mN·cm/cm$^2$ or greater and a compression recovery rate of 40% or greater.

BRIEF DESCRIPTION OF DRAWINGS

FIG. 5 is an enlarged plan view illustrating, under further magnification, a portion of the composite sheet illustrated in FIG. 4.

FIG. 6 shows enlarged cross-sectional views each illustrating a cross section along the thickness direction of the topsheet (composite sheet) illustrated in FIG. 3, wherein

DESCRIPTION OF EMBODIMENTS

Recent studies report that various tactile stimulations arouse pleasant sensations causing a comfortable feel. For example, Non-Patent Literature 1 reports that tactile stimulation imparted by stroking the skin with a brush member for causing a pleasant sensation is transmitted to the brain by C nerve fibers and arouses a pleasant sensation. Non-Patent Literature 2 reports that cupping and touching the skin of the face with the palms with eyes closed arouses pleasant sensations such as a feeling of happiness, a feeling of satisfaction, a luxurious feel, and a good feeling of tension.

Non-Patent Literature 3 reports that massaging, which is a type of tactile stimulation that arouses a pleasant sensation, increases the amount of oxytocin inside the body, thereby arousing a pleasant sensation. Oxytocin is a peptide hormone that is produced mainly in the hypothalamus of the brain. Non-Patent Literature 4 reports that an increase in the amount of oxytocin in the body by nasal administration of oxytocin increases pleasant sensations caused by tactile sensation.

However, there have been no studies on configurations for increasing the amount of oxytocin by tactile stimulation in absorbent articles such as disposable diapers.

The present invention concerns the provision of an absorbent article that can easily offer a pleasant sensation to a user, such as a wearer, when the user touches a sheet.

Inventors have found that a pleasant sensation can easily be produced by contact with a projecting-and-depressed sheet having projections and depressions, wherein the projections are easily deformable, and, when the user's skin moves back and forth while in contact with the projecting-and-depressed sheet, the projections easily follow the movement of the skin in both the forward path and the return path. Such a projecting-and-depressed sheet can suitably be used as a constituent member of an absorbent article.

The present invention is described below according to preferred embodiments thereof with reference to the drawings.

Figure 1:
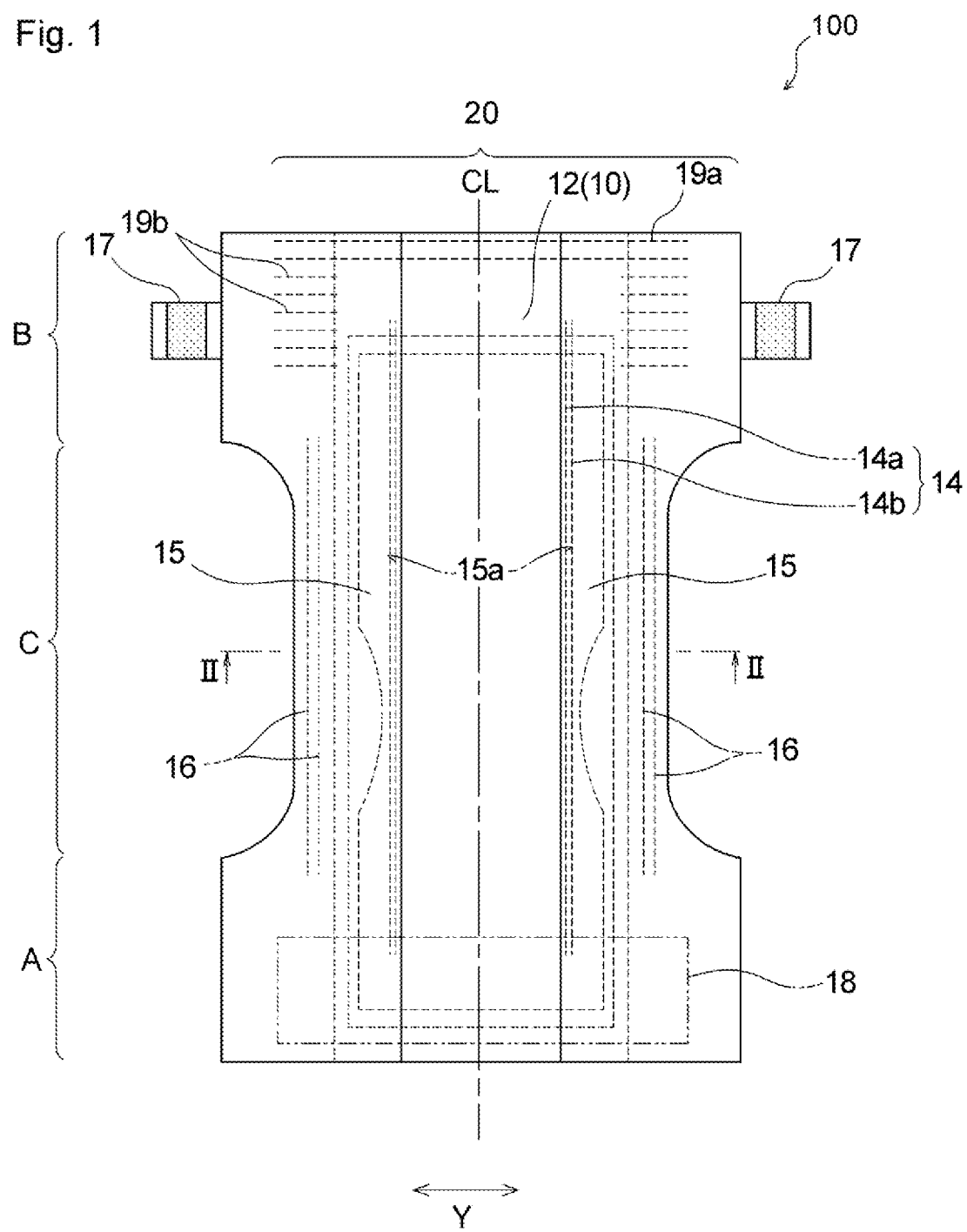
FIG. 1 is a plan view of a topsheet side, i.e., a skin-facing surface side, illustrating a spread-open state (spread-open and stretched state) wherein a disposable diaper, which is an embodiment of an absorbent article of the present invention, has been spread in a planar state by stretching elastic members in various parts.
Figure 2:
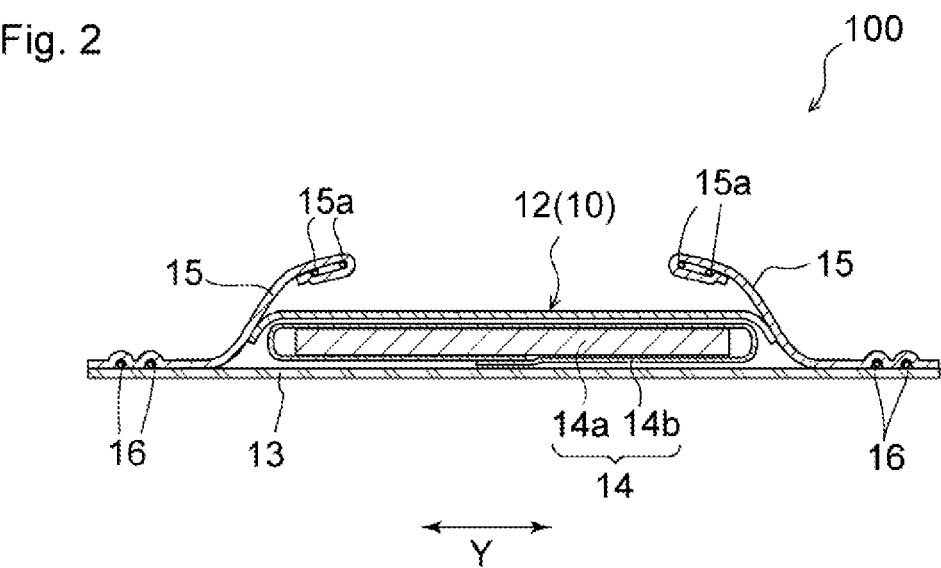
FIG. 2 is a cross-sectional view taken along line II-II of FIG. 1.

FIGS. 1 and 2 illustrate a basic structure of a disposable diaper 100 (also simply called "diaper 100") which is an embodiment of an absorbent article of the present invention.

As illustrated in FIGS. 1 and 2, the diaper 100 includes: a liquid-permeable topsheet 12; a liquid-impermeable backsheet 13; and an absorbent member 14 arranged between the two sheets 12, 13. In relation to the backsheet 13, "liquid-impermeable" is a concept encompassing "sparingly liquid-permeable"; the concept also encompasses cases where the backsheet 13 does not allow passage of liquid at all, and cases where the backsheet is made of a water-repellent sheet etc.

In a spread-open state where the diaper 100 is spread out in a plane as illustrated in FIG. 1, the diaper 100 has: a longitudinal direction X corresponding to the front-rear direction of a wearer; and a width direction Y orthogonal to the longitudinal direction X. The longitudinal direction of the later-described projecting-and-depressed sheet 10 matches the longitudinal direction X of the diaper 100.

The diaper 100 includes, in the longitudinal direction X: a front portion A to be arranged on the wearer's front side when the diaper is worn; a rear portion B to be arranged on the wearer's rear side when the diaper is worn; and a crotch portion C located between the front portion A and the rear portion B. That is, the longitudinal direction X of the diaper 100 corresponds to the direction extending from the front portion A toward the rear portion B via the crotch portion C. More specifically, the longitudinal direction X is the direction extending from a section to be arranged on the wearer's front side toward a section to be arranged on the rear side via a section to be arranged in the crotch, and generally matches the longitudinal direction of the absorbent member 14 and the longitudinal direction of the absorbent core 14a.

The diaper 100 is an open-type disposable diaper; fastening tapes 17 are provided to the respective lateral side edge portions of the rear portion B, and a landing zone 18 for fastening the fastening tapes 17 is provided on the outer surface of the front portion A. Each fastening tape 17 includes an attachment portion to be fastened to the landing zone 18. The attachment portion may be, for example, an adhesive portion formed by applying an adhesive to a tape base material. For the tape base material, it is possible to use one of various known materials such as nonwoven fabrics.

The absorbent member 14 in the diaper 100 includes an absorbent core 14a, and a core-wrap sheet 14b enveloping the absorbent core 14a. The absorbent core 14a may be made of, for example, a fiber stack including a liquid-absorbing fiber such as pulp fiber, or a mixed fiber stack including a liquid-absorbing fiber and a water-absorbent polymer. Examples of the liquid-absorbing fiber include cellulose-based hydrophilic fibers, such as pulp fiber, rayon fiber, cotton fiber, and cellulose acetate. Other than cellulose-based hydrophilic fibers, it is also possible to use fiber made of a synthetic resin, such as a polyolefin, a polyester, or a polyamide, and hydrophilized by a surfactant, for example. For the core-wrap sheet 14b, it is possible to use, for example, tissue paper or a water-permeable nonwoven fabric. A single core-wrap sheet 14b may envelop the entire absorbent core 14a, or two or more sheets may be used in combination to envelop the absorbent core 14a. For the backsheet 13, it is possible to use, for example, a liquid-impermeable or water-repellent resin film, or a laminate sheet of a resin film and a nonwoven fabric.

Leak-proof-cuff-forming sheets 15, each including elastic members 15a, are provided to each of both sides, along the longitudinal direction X, of the diaper 100, and, by contraction of the elastic members 15a, leak-proof cuffs that stand up toward the wearer's skin side are formed in the crotch portion C in a state where the diaper is worn. In sections surrounding the legs in the crotch portion C, leg-portion elastic members 16 are provided in a stretched state, and by contraction of the leg-portion elastic members, leg gathers that improve fittability around the wearer's legs are formed in the crotch portion C in a state where the diaper is worn.

Figure 3:
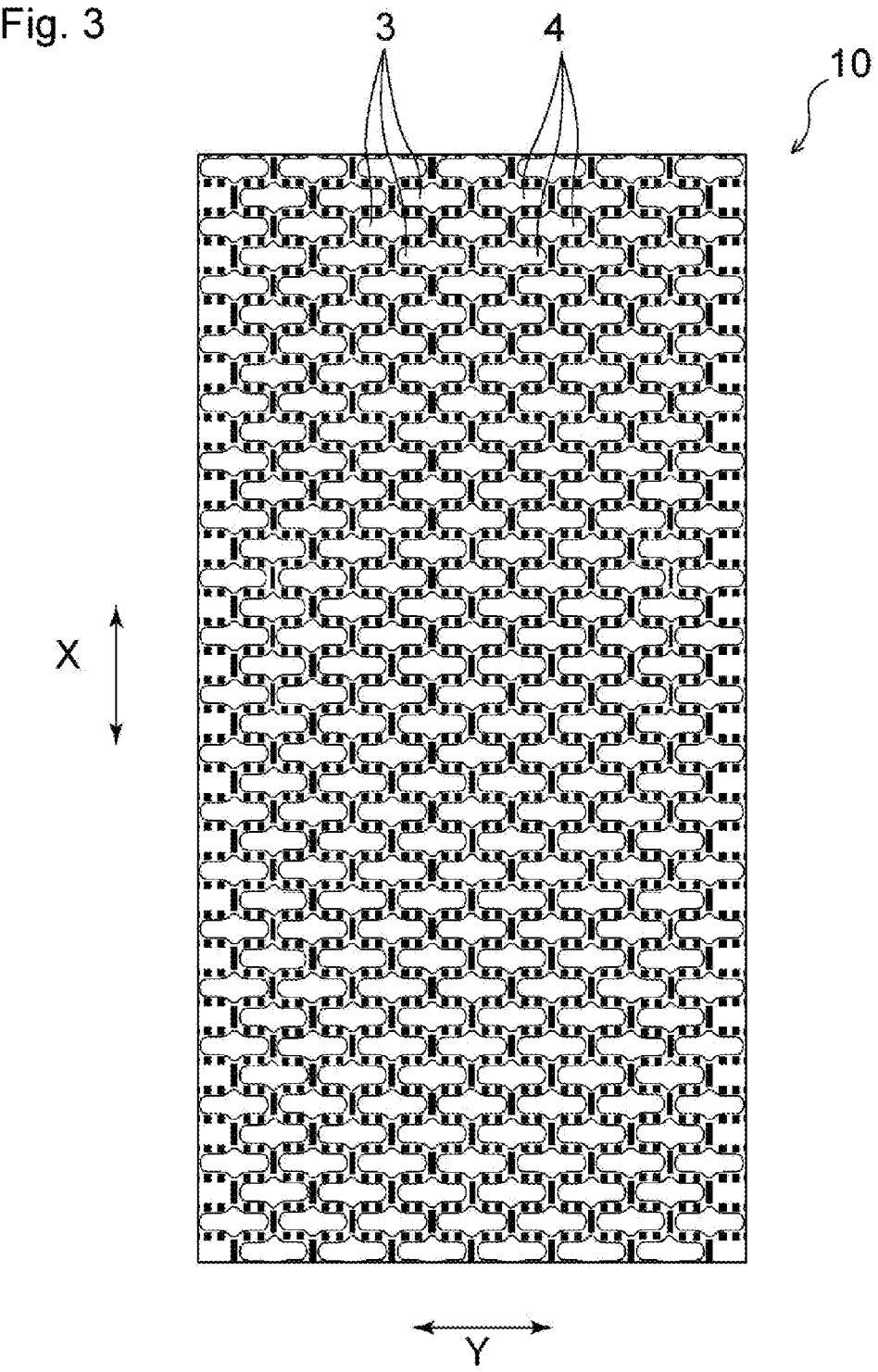
FIG. 3 is a plan view illustrating a topsheet (projecting-and-depressed sheet) of the disposable diaper of the first embodiment.
Figure 4:
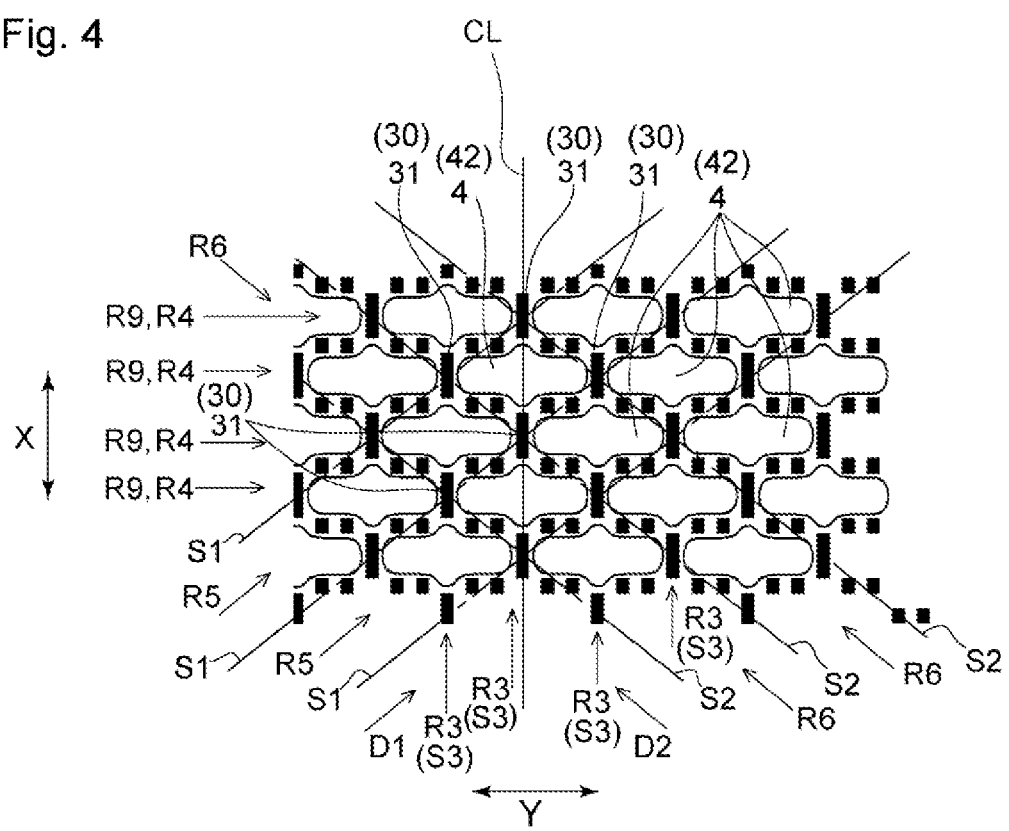
FIG. 4 is an enlarged plan view illustrating a portion of a composite sheet used as a topsheet in the first embodiment.

The diaper 100 includes a projecting-and-depressed sheet 10 as a constituent member. The projecting-and-depressed sheet 10 has a plurality of depressions and projections on a skin-facing surface to be brought into contact with the wearer's skin. In the present embodiment, the topsheet 12 is the projecting-and-depressed sheet 10, and, as illustrated in FIGS. 3 to 5, a plurality of depressions 3 and projections 4 are formed on the skin-facing surface of the topsheet 12. In the present embodiment, the depressions 3 are formed in sections of the later-described joined portions 30.

In the Description, the "skin-facing surface" refers to a surface of the diaper 100, which is an absorbent article, or a constituent member thereof (e.g., the topsheet 12), facing the wearer's skin side when the diaper is worn—i.e., on the side relatively closer to the wearer's skin. The "non-skin-facing surface" refers to a surface of the diaper 100, or a constituent member thereof, facing the opposite side from the skin (i.e., the clothing side) when the diaper is worn—i.e., on the side relatively farther from the wearer's skin. Herein, "when worn" refers to a state in which the diaper 100 is maintained in its ordinary, proper wearing/attachment position—i.e., the correct wearing/attachment position of the diaper.

FIG. 4 is an enlarged plan view illustrating a portion of the projecting-and-depressed sheet 10. FIG. 5 is an enlarged plan view illustrating, under further magnification, a portion of the projecting-and-depressed sheet 10.

As illustrated in FIGS. 4 and 5, the skin-facing surface of the projecting-and-depressed sheet 10 has a plurality of projections 4 formed so as to project toward the wearer's skin side, and also has a plurality of depressions 3 located between the projections 4. In contrast, the non-skin-facing surface of the projecting-and-depressed sheet 10 is flat.

Figure 6A:
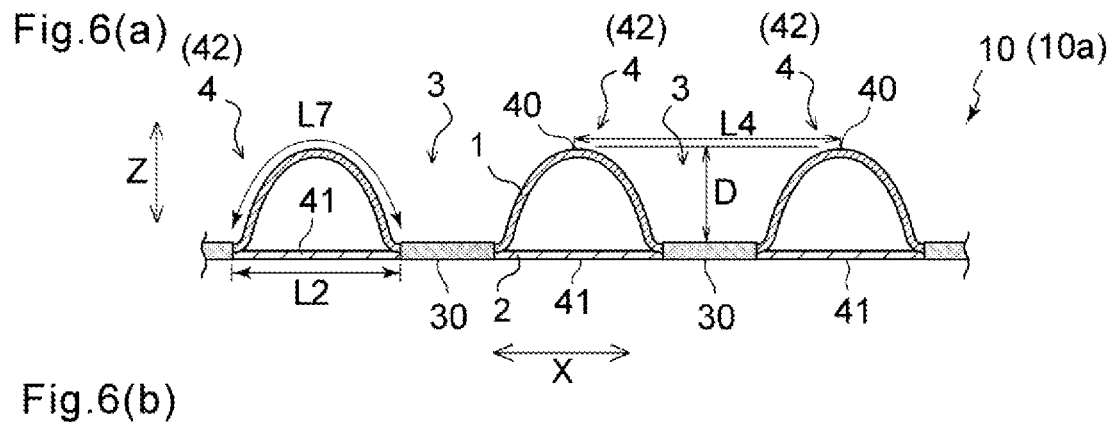
FIG. 6(a) is a schematic cross-sectional view taken along line of FIG. 5.
Figure 6B:
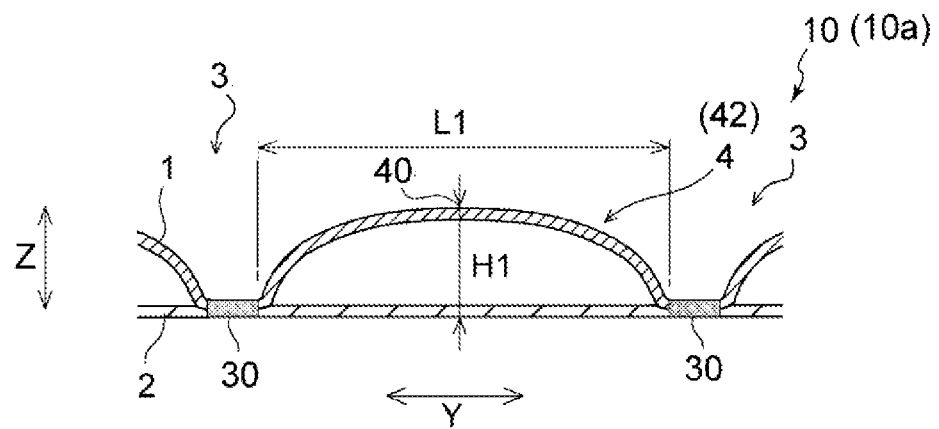
FIG. 6(b) is a schematic cross-sectional view taken along line Iv-Iv of FIG. 5.

FIGS. 6(a) and 6(b) are schematic cross-sectional views of projections 4 in the thickness direction Z of the projecting-and-depressed sheet.

In the projecting-and-depressed sheet 10, the respective apexes 40 of the projections 4 on the sheet are movable along a given direction, and the movable range, in the given direction, of the apex 40 of each projection 4 is 30% or greater to the length L2 of a bottom portion 41 of the projection 4. Making the apex 40 of the projection 4 movable in the given direction contributes to offering a comfortable feeling and arousing a pleasant sensation. The movable range of the apex 40 of each projection 4 is preferably 35% or greater, more preferably 45% or greater, and preferably 100% or less, more preferably 85% or less, and preferably from 35 to 100%, more preferably from 45 to 85%.

The "given direction" is the direction in which the apex 40 of the projections 4 can move, and may be, for example, the longitudinal direction X, the width direction Y, or a direction intersecting therewith, within the plane of the diaper. It is preferable that the apex 40 of each projection 4 of the projecting-and-depressed sheet 10 is movable at least in the longitudinal direction X, and the movable range of the apex of each projection 4, in at least the longitudinal direction X, is preferably within the aforementioned range. For example, the movable range of the apex of each projection 4 may be within the aforementioned range in the longitudinal direction X and also in a direction at a predetermined angle—e.g., at an angle less than 45°—to the longitudinal direction X. The length L2 (see FIG. 6(*a*)) of the bottom portion 41 of each projection 4 in the given direction is the maximum length of the bottom portion 41 in the given direction. The "given direction" regarding the movable range F of the projection 4 matches the "given direction" regarding the length L2 of the bottom portion 41 of the projection 4. FIG. 6(*a*) illustrates the length of the projection 4's bottom portion 41 in the longitudinal direction X as the length L2 of the projection 4's the bottom portion 41 in the given direction.

The apex 40 of the projection 4 is the section of the projection 4 closest to the wearer's skin, as illustrated in FIG. 6(*a*), and, when the skin-facing surface is arranged upward and the non-skin-facing surface is arranged downward, the apex is the section located at the highest position in the thickness direction Z of the projecting-and-depressed sheet. The expression "the apex 40 of the projection 4 moves in a given direction" means that, when the apex 40 of the projection 4 is placed in contact with a contact target such as the wearer's skin and the contact target moves along a given direction, the apex 40 moves along the given direction following the movement of the contact target.

The movable range of the apex 40 of each projection 4 is the length over which the apex 40 of the projection 4 can move in the given direction, and can be measured according to the following method.

{Method for Measuring Movable Range of Apex of Projection}

Figure 7A:
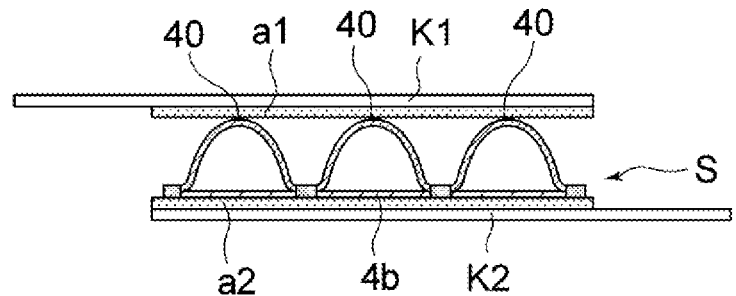
FIGS. 7(a) and 7(b) are diagrams illustrating a method for measuring a movable range of an apex of a projection.
Figure 7B:
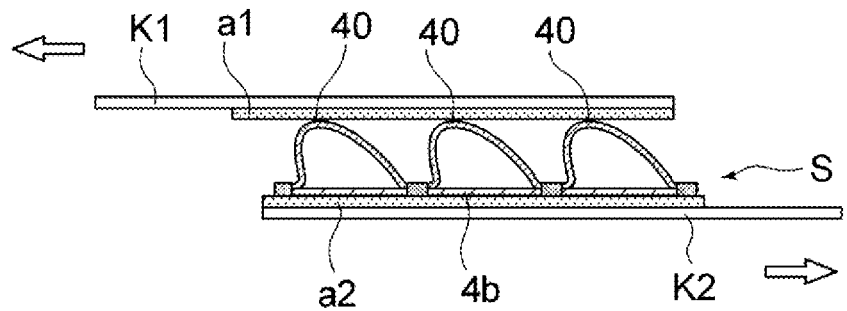

A method for measuring the movable range of the apex of each projection is described with reference to FIGS. 7(*a*) and 7(*b*).

First, a test piece S that is rectangular in a planar view and that is 50 mm long in the longitudinal direction and 30 mm long in the width direction is cut out from a region of the projecting-and-depressed sheet where a plurality of projections are formed. Next, two pieces of movable plates K are prepared, each movable plate being made by superposing, on a PET film b (product name Star OHP Film from Star Syoji Corporation), an adhesive tape a (product name No. 500 from Nitto Denko Corporation) having the same shape and size as the test piece S. Then, the non-skin-facing surface of the test piece S is superposed and fixed onto one movable plate K2 in a state opposing the surface of the movable plate K2 having the adhesive tape a2 (see FIG. 7(*a*)). The movable plate K2 and the test piece S are fixed together by moving a 1-kg roller over the test piece back and forth five times, to compression-bond the adhesive tape of the movable plate K2 and the test piece together. Then, the skin-facing surface of the test piece S is compression-bonded at 0.5 to 10 kPa in a state opposing the surface of the movable plate K1 having the adhesive tape a1, thereby obtaining a measurement sample. At this time, the adhesive tape and the test piece S are compression-bonded by adjusting the load so that the thickness of the test piece S is reduced to 60 to 80% of the thickness before being fixed. In this way, the respective apexes of the projections of the test piece S are bonded to the movable plate K1 through the adhesive tape a1. Next, the two movable plates K, to which the test piece S has been fixed, are attached to a tensile tester (Autograph AG-X from Shimadzu Corporation) at a chuck-to-chuck distance of 100 mm. At this time, the test piece is attached so that the movement direction, in which the respective apexes of the projections are to be moved, matches the tensile direction of the tensile tester. The movable plates K are attached to the tensile tester such that the respective sections to be attached are located at the center in the thickness direction of the test piece. The two movable plates K1, K2 are pulled in mutually opposite directions at 100 mm/minute, and the tensile strength (N), which changes with tensile distance, is measured, to thereby find the tensile distance M when the tensile strength reaches 6.0 N. When the length of each projection's bottom portion in the tensile direction of the test piece S is defined as L2, the movable range F (%) of the apex of each projection is calculated according to the following equation (1). Measurement is repeated three times, and the average value is found as the movable range of the apex of the projection.

$$F(\%)=(M\times 2/L2)\times 100 \tag{1}$$

{Measurement of Length of Bottom Portion of Projection}

The length L2, in the given direction, of the bottom portion 41 of the projection 4 is measured according to the following method.

In a planar view of the skin-facing surface of the projecting-and-depressed sheet, the projecting-and-depressed sheet is cut with a sharp razor along a line parallel to the given direction, and the cut cross-section is observed with a microscope (e.g., Digital Microscope VHX-1000 from Keyence Corporation) under a magnification of 10× to 100×. The outline of the surface of the projection within the cut cross-section is specified, to thereby measure the distance between a start point and an endpoint of a line forming the projection's outline along the same direction as the given direction (see FIG. 6(*a*)). The distance between the start point and the endpoint is measured at a position, in the projection's thickness direction, at which the length between the start point and the endpoint becomes the longest in the given direction. The distance is measured for at least five projections, and the average value is found as the length L2 of the bottom portion of the projection.

The skin-facing surface of the projecting-and-depressed sheet 10 has the following surface properties (friction coefficient MIU and difference in friction coefficient between the forward path and return path when moved back and forth along a given direction). In cases where the projecting-and-depressed sheet 10 includes a plurality of regions respectively including the depressions 3 and projections 4 formed according to mutually different patterns, it is preferable that at least a portion of the plurality of regions has the surface properties described below.

On the skin-facing surface of the projecting-and-depressed sheet 10, the mean friction coefficient MIU in a given direction is 0.3 or less, and preferably 0.1 or greater, and preferably 0.27 or less, more preferably 0.24 or less. On the skin-facing surface of the projecting-and-depressed sheet 10, it is preferable that the mean friction coefficient MIU in the longitudinal direction X is within the aforementioned range.

On the skin-facing surface of the projecting-and-depressed sheet 10, the difference in friction coefficient between the forward path and the return path when moved back and forth along a given direction is less than 0.1, and preferably 0.001 or greater, and preferably 0.07 or less, more preferably 0.04 or less. On the skin-facing surface of the projecting-and-depressed sheet 10, it is preferable that the difference in friction coefficient between the forward path and the return path when moved back and forth along the longitudinal direction X is within the aforementioned range.

The mean friction coefficient MIU and the difference in friction coefficient between the forward path and the return path are measured according to the following methods. The mean friction coefficient MIU, as well as the work of compression WC and the compression recovery rate RC described further below, are measured using KES-FB4-AUTO-A (product name) from Kato Tech Co., Ltd. according to the method described in the following book:

Sueo Kawabata, "Standardization and Analysis of Texture Evaluation", 2nd edition, Texture Measurement and Standardization Committee, The Textile Machinery Society of Japan (Jul. 10, 1980).

{Methods for Measuring Friction Coefficient MIU and Difference in Friction Coefficient Between Forward Path and Return Path}

A test piece that is 20 cm long in the longitudinal direction and 10 cm long in the width direction is cut out from a region of the projecting-and-depressed sheet where a plurality of projections are formed. The test piece is placed, with its skin-facing surface facing up, on a test stage having a flat, smooth metal surface. Then, a contact is moved back and forth along the longitudinal direction of the test piece while keeping the contact and the test piece in contact with one another. More specifically, the test piece is moved horizontally over a distance of 2 cm at a constant speed of 0.1 cm/sec while pressing the contact surface of the contact against the skin-facing surface of the test piece with a force of 49 cN. At this time, a uniaxial tension of 19.6 cN/cm is applied to the test piece. The contact is made of twenty 0.5-mm-dia. piano lines arranged side by side, thus having a width of 10 mm, and is bent into a U-shape. The contact is pressed against the test piece with a force of 49 cN by using a weight. The respective friction coefficients in both the forward path and the return path in the back-and-forth movement of the contact are measured, and a mean value, i.e., friction coefficient MIU, is calculated from equation (2) below. In the equation (2) below, the friction coefficient in the forward path is $MIU_{MD1}$ and the friction coefficient in the return path is $MIU_{MD2}$.

Mean friction coefficient $MIU = \{(MIU_{MD1}^2 \pm MIU_{MD2}^2)/2\}^{1/2}$ (2).

The projecting-and-depressed sheet 10 has the following physical properties. In cases where the projecting-and-depressed sheet 10 includes a plurality of regions respectively including the depressions 3 and projections 4 formed according to mutually different patterns, it is preferable that at least a portion of the plurality of regions has the following physical properties (work of compression WC and compression recovery rate RC).

The projecting-and-depressed sheet 10 has a work of compression WC of 2.0 mN·cm/cm² or greater, preferably 2.5 mN·cm/cm² or greater, more preferably 3.5 mN·cm/cm² or greater, and preferably 20 mN·cm/cm² or less. The work of compression serves as a scale for evaluating the cushioning properties of the projecting-and-depressed sheet; it can be evaluated that, the greater the WC value, the higher the cushioning properties.

The projecting-and-depressed sheet 10 has a compression recovery rate RC of 40% or greater, preferably 46% or greater, more preferably 52% or greater, and preferably 85% or less. The compression recovery rate serves as a scale indicating the degree of recovery when the projecting-and-depressed sheet is first compressed and then the compressed state is released. It can be evaluated that, the greater the RC value, the higher the compression recovery properties.

The work of compression and the compression recovery rate are measured according to the following methods.

{Methods for Measuring Work of Compression WC and Compression Recovery Rate RC}

A test piece that is 20 cm long in the longitudinal direction and 10 cm long in the width direction is cut out from a region of the projecting-and-depressed sheet where a plurality of projections are formed, and the test piece is placed on a test stage. Next, the test piece is compressed between steel plates each having a circular surface with an area of 2 cm². The compression speed is 0.02 cm/sec, and the maximum compression load is 50 g/cm². Measurement in the recovery process is also conducted at the same speed. The work of compression (WC) and the work of recovery (WC') are expressed by the equations below. The work of recovery (WC') indicates the energy for when the test piece returns to its original state from its compressed state. In the equations, Tm and To respectively indicate the thickness at a load of 49 cN/cm² and the thickness at a load of 0.49 cN/cm². In the equations, Pa indicates the load (cN/cm²) during measurement (compression process), and Pb indicates the load (cN/cm²) during measurement (recovery process).

The compression recovery rate (RC) is the ratio between the work of compression (WC) during compression and the work of recovery (WC') when the test piece is returned to its original state from its compressed state, and is expressed as [WC'/WC]×100.

$$WC = \int_{T_0}^{T_m} P_a dT \quad \text{[Math. 1]}$$

$$WC' = -\int_{T_m}^{T_0} P_b dT \quad \text{[Math. 2]}$$

When the diaper 100 is worn, the projecting-and-depressed sheet 10 will be in contact with the wearer's skin. Also, a parent/guardian or caregiver of the wearer may touch the projecting-and-depressed sheet 10 when putting the diaper 100 on the wearer. For example, the parent/guardian or caregiver may touch the projecting-and-depressed sheet 10 when adjusting/straighten up sections around the legs of the diaper 100 while sliding his/her fingers along the longitudinal direction X.

The projecting-and-depressed sheet 10 having the aforementioned surface properties and physical properties has projections 4 that project toward the wearer's skin side, and the apex 40 of each projection 4 is movable in a given direction within a predetermined range. In this projecting-and-depressed sheet, the projections themselves are easily deformable, and, when the skin of the user, such as the wearer or parent/guardian, is in contact with the projecting-and-depressed sheet and the user's skin moves back and forth in this state, the projections easily follow the movement of the skin in both the forward path and the return path. Inventors have found that such contact between the projecting-and-depressed sheet and the user's skin creates tactile stimulation which thereby increases the amount of oxytocin of the user. Stated differently, Inventors have found that, when the user touches the projecting-and-depressed sheet 10, the amount of oxytocin increases, thereby arousing a pleasant sensation in the user.

The projecting-and-depressed sheet 10, having the aforementioned configuration, provides fluffy softness, smoothness along the longitudinal direction X, and comfortable texture, which are considered as contributing to the arousal of a pleasant sensation. It should be noted that tests have verified that napped fabric, such as velvet, is soft, but does not have the aforementioned configuration of the projecting-and-depressed sheet, and thus does not increase the amount of oxytocin (see Comparative Example 3 below). The aforementioned pleasant sensation is expressed as an increase in the amount of oxytocin measured according to a specific method. "Pleasant sensation" encompasses such feelings as a feeling of happiness, feeling of satisfaction, luxurious feel, and good feeling of tension.

In addition to the aforementioned comfortable texture, the projecting-and-depressed sheet 10 has excellent conformability to changes in movement or orientation of the legs along the longitudinal direction X. This can thus lessen the burden on the wearer's skin.

In the projecting-and-depressed sheet 10 of the present embodiment, the entire region constitutes a projecting-and-depressed region including the projections having the aforementioned configuration. The projecting-and-depressed region, however, may be formed only in a section of the projecting-and-depressed sheet in the absorbent article's longitudinal direction; for example, the projecting-and-depressed region may be formed only in the crotch portion C, only in the front portion A, only in the rear portion B, or in the crotch portion C and either the front portion A or the rear portion B. The projecting-and-depressed sheet 10 may include a projecting-and-depressed region including a plurality of regions respectively having depressions and projections formed according to mutually different patterns. In this case, it will suffice if at least a portion of the plurality of regions includes the projections having the aforementioned configuration.

The projecting-and-depressed sheet 10 in the diaper 100 of the present embodiment is a composite sheet 10a including a first sheet 1 and a second sheet 2 that are layered on one another and that are joined together at a plurality of joined portions 30. Stated differently, the topsheet 12 of the diaper 100 is a composite sheet 10a.

The first sheet 1 forms the projections 4 that project in a direction separating from the second sheet 2 at sections other than the joined portions 30. With this configuration, it is possible to improve the smooth feel caused by making the apex 40 of each of the projections 4 movable.

From the viewpoint of allowing the apex 40 of the projections 4 to move more easily in the longitudinal direction X and making the feel smoother as well as improving texture by reducing friction with the skin, it is preferable that the projection 4's outer peripheral length L7 (see FIG. 6(a)), in the given direction of the projecting-and-depressed sheet 10, along the projection 4's surface within a cross section in the thickness direction is preferably 1.2 times or greater, more preferably 1.3 times or greater, even more preferably 1.4 times or greater, and preferably 3 times or less, more preferably 2.5 times or less, even more preferably 2 times or less, and preferably from 1.2 to 3 times, more preferably from 1.3 to 2.5 times, even more preferably from 1.4 to 2 times, the length L2, in the given direction, of the bottom portion 41 of the projection 4. Hereinafter, the outer peripheral length L7, in the given direction of the projecting-and-depressed sheet 10, along the projection 4's surface within a cross section in the thickness direction is also called "outer peripheral length L7". The "given direction" regarding the outer peripheral length L7 of the projection 4 matches the "given direction" regarding the length L2 of the bottom portion 41 of the projection 4. In FIG. 6(a), the projection 4's outer peripheral length in the longitudinal direction X is illustrated as the projection 4's outer peripheral length L7 in the given direction.

The outer peripheral length L7 can be found by measuring the length of a line forming the outline of the projection's surface as specified in the aforementioned {Measurement of Length of Bottom Portion of Projection}. The measurement is performed for at least five projections, and the average value is found as the outer peripheral length L7.

From the viewpoint of making the projecting-and-depressed sheet feel smoother as well as improving texture by reducing friction with the skin, it is preferable that the length L4 (see FIG. 6(a)) between respective apexes 40 of the projections 4 adjacent to one another in a given direction is preferably 0.5 times or greater, more preferably 1 time or greater, even more preferably 1.5 times or greater, and preferably 5 times or less, more preferably 4 times or less, even more preferably 3 times or less, and preferably from 0.5 to 5 times, more preferably from 1 to 4 times, even more preferably from 1.5 to 3 times, the depth D (see FIG. 6(a)) of the depression 3 located between those projections 4. The "given direction" regarding the outer peripheral length L7 of the projection 4 matches the "given direction" regarding the length L4 between respective apexes 40 of the projections 4. FIG. 6(a) illustrates projections 4 adjacent to one another in the longitudinal direction X as projections 4 adjacent to one another in the given direction.

The length L4 between respective apexes 40 of the projections 4 is obtained by first finding, as the apex, the highest section in the cross section of each projection as observed in the aforementioned {Measurement of Length of Bottom Portion of Projection}, and measuring the length between respective apexes of projections adjacent to one another in a given direction. The measurement is performed for at least five sets of adjacent projections, and the average value is found as the length L4 between respective apexes 40 of the projections 4.

The depth D of the depression 3 located between the projections 4 is the length, in the projecting-and-depressed sheet's thickness direction, between the apex of each projection and the bottom portion of the depression, and is found by observing the apex of the projection and the bottom portion of the depression according to the aforementioned {Measurement of Length of Bottom Portion of Projection}. The measurement is performed for respective depressions located between at least five sets of adjacent projections, and the average value is found as the depth D of the depression 3.

Figure 8:
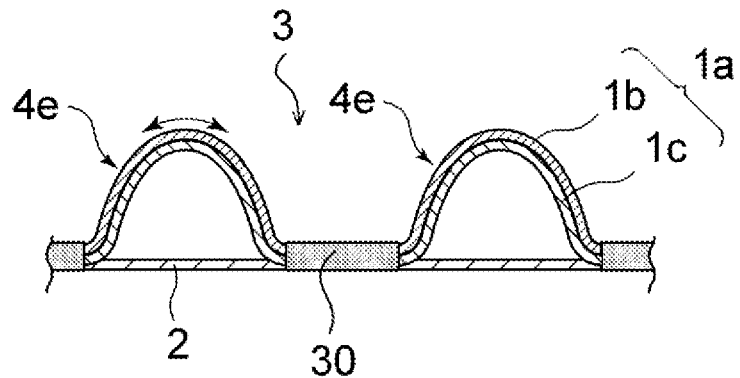
FIG. 8 is a diagram corresponding to FIG. 6(a), illustrating a main portion of another embodiment of the present invention.

As illustrated in FIG. 6(a), the first sheet forming the projections 4 in the composite sheet 10a may have a single-layer structure, or may have a multilayer structure in which a plurality of layers are layered, as illustrated in FIG. 8.

The first sheet 1a illustrated in FIG. 8 includes a first layer 1b on the skin-facing surface side and a second layer 1c on the non-skin-facing surface side, and both the first and second layers 1b, 1c form the projections 4e projecting toward the skin-facing surface side.

It is preferable that the second layer 1c includes first fibers and second fibers satisfying at least one of the conditions (1) to (4) described below, and the second layer 1c includes a larger amount of the second fibers than the first layer 1b. With this configuration, the degree of freedom of the movement of constituent fibers can be made different between the skin-facing surface and the non-skin-facing surface of the composite sheet 10a, thereby allowing the projections 4 formed on the skin-facing surface to deform easily and improving the smooth feel and fluffiness of the projecting-and-depressed sheet.

(1) The melting point of a constituent component of the second fibers is higher than that of a constituent component of the first fibers.
(2) The fiber diameter of the second fibers is greater than that of the first fibers.
(3) The second fibers are crimped fibers having a greater number of crimps than the first fibers.
(4) The first fibers and the second fibers are core-sheath conjugate fibers, wherein the diameter ratio of a sheath component in the core-sheath conjugate fiber constituting the second fibers is lower than that of the first fibers.

In cases of satisfying the aforementioned condition (1), from the viewpoint of increasing the degree of freedom of movement of fibers by suppressing fusion-bonding between the first fibers and the second fibers, it is preferable that the difference in melting point between the respective constituent components of the first fibers and the second fibers is preferably 10° C. or greater, more preferably 20° C. or greater, and preferably 100° C. or less, more preferably 60° C. or less, and preferably from 10° C. to 100° C., more preferably from 20° C. to 60° C.

It is preferable that the first fibers and the second fibers are fibers having a core-sheath structure, and the melting point of the respective sheath components of the first fibers and the second fibers is lower than the melting point of the respective core components of both the first fibers and the second fibers, and it is also preferable that the difference in melting point between the respective sheath components of the first fibers and the second fibers satisfies the aforementioned range.

The melting point of the constituent component of the fibers is measured according to the following method.

{Method for Measuring Melting Point of Constituent Component of Fiber}

A finely-cut fiber sample is subjected to thermal analysis by using a differential scanning calorimeter (DSC 6200 from Seiko Instruments Inc.) at a temperature rise rate of 10° C./min, to measure the peak melting temperatures of the constituent components of the fibers. This measurement is performed for fiber samples (sample weight: 2 mg) taken out from ten discretionary sites in each of the first layer and the second layer of the first sheet; the lowest peak melting temperature is defined as the melting point of the constituent component of the first fibers, and the second lowest peak melting temperature is defined as the melting point of the constituent component of the second fibers.

When the content of the second fibers in the first layer is defined as f1 and the content of the second fibers in the second layer is defined as f2, the ratio (f2/f1) of f2 to f1 satisfying the aforementioned condition (1) is found on the basis of the respective melting points of fibers included in measurement pieces taken out from each of the first layer and the second layer, by determining whether the fibers are either first fibers or second fibers. First, a 2-mm square measurement piece is cut out from each of the first layer and the second layer of the first sheet, and the respective peak melting temperatures of constituent components of the fibers included in each measurement piece are found according to the aforementioned method. Fibers, whose peak melting temperature of the constituent component is close to the melting point of the constituent component of the second fibers as found according to the aforementioned method, are determined as the second fibers, whereas fibers whose peak melting temperature is close to the melting point of the constituent component of the first fibers are determined as the first fibers. Herein, "close to the melting point" means that the difference from the melting point is within 3° C. This measurement is performed for each of the first layer and the second layer, and the content ratio of the second fibers included in each of the first layer and the second layer is found from the melt fraction at the melting temperature of the second fibers. Measurement is repeated three times, and the average value is found as the aforementioned ratio f2/f1.

Scissors and tweezers are used when taking out fibers from the first layer or the second layer of the first sheet to determine the conditions (1) to (4). Fibers are taken out from the surface (outermost face) of each of the first layer and the second layer. In cases where different fiber layers are clearly visible in terms of fiber amount, fiber diameter, core-sheath ratio, appearance (whiteness etc.), etc., the first and second layers can be distinguished by visually observing the cross section of the first sheet with a microscope or an electron microscope (SEM). In cases where the first sheet includes fiber layers that visually have clear differences, such as including fibers with different fiber diameters or fiber shapes, the interface between the fiber layers, respectively having different fiber diameters or shapes, is observed with a SEM and defined as the boundary, and the fiber layers are distinguished by the boundary. In cases where there is visually no clear difference, the thickness of the nonwoven fabric is measured by observing the nonwoven fabric's cross section with a microscope (VHX-1000 from Keyence Corporation), and the thickness is divided into two equal parts, wherein one is defined as the first layer and the other is defined as the second layer.

For the first fibers and second fibers satisfying the aforementioned condition (1), it is possible to suitably use, for example, fusion-bondable fibers, and particularly fibers made of thermoplastic polymer materials. Examples of thermoplastic polymer materials include polyolefins such as polyethylene or polypropylene, polyesters such as polyethylene terephthalate, and polyamides. Core-sheath conjugate fibers including a combination of such thermoplastic polymer materials (e.g., fibers including polyethylene terephthalate or polypropylene as the core component and polyethylene as the sheath component) may also be used, and the combination can be selected such that the melting point of the respective sheath components of the first fibers and the second fibers is lower than the melting point of the respective core components of both the first fibers and the second fibers, and the difference in melting point between the respective sheath components of the first fibers and the second fibers satisfies the aforementioned range.

In cases of satisfying the aforementioned condition (2), from the viewpoint of increasing the degree of freedom of movement of fibers by reducing the number of fusion-bonded points between the fibers, it is preferable that the fiber diameter of the second fibers is preferably 1.5 times or greater, more preferably 2 times or greater, and preferably 6 times or less, more preferably 4 times or less, and preferably from 1.5 to 6 times, more preferably from 2 to 4 times, the fiber diameter of the first fibers. The fiber diameter of the respective fibers is measured according to the following method.

{Method for Measuring Fiber Diameter}

The first sheet, which is the measurement object, is cut with a razor (e.g., a single-edged razor from Feather Safety Razor Co., Ltd.), to obtain a measurement piece having a rectangular (8×4 mm) planar-view shape. When cutting the measurement object, care is taken so as not to destroy, by pressure etc. upon cutting, the structure of the cut surface of the measurement piece being formed by cutting. A preferable method for cutting the measurement object is to immerse the measurement object in liquid nitrogen and sufficiently freeze the measurement object before cutting, and then cutting the measurement object. Then, with a double-faced paper tape (Nicetack NW-15 from Nichiban Co., Ltd.), the measurement piece is bonded to a sample stage. The measurement piece is then subjected to platinum coating. The coating is performed using an ion sputtering device E-1030 (product name) from Hitachi Naka Seiki, Ltd., with a sputtering time of 30 seconds. The cut surface of the measurement piece is observed at a magnification of 1000× with an S-4000 field emission scanning electron microscope from Hitachi, Ltd. From the electron microscope image, the boundary between the first and second layers is determined from the difference in fiber diameter, and for ten pieces of fibers in each layer, the length in the width direction with respect to the fiber's length direction is measured, and the average value is found as the fiber diameter. Note that, the average value of three largest fiber diameters is found as the fiber diameter of the second fibers, and the average value of three smallest fiber diameters is found as the fiber diameter of the first fibers.

When the content of the second fibers in the first layer is defined as f1 and the content of the second fibers in the second layer is defined as f2, the ratio (f2/f1) of f2 to f1 satisfying the aforementioned condition (2) is found on the basis of the respective fiber diameters of fibers included in measurement pieces taken out from each of the first layer and the second layer, by determining whether the fibers are either first fibers or second fibers. First, a 4-mm square measurement piece is cut out from each of the first layer and the second layer of the first sheet, and the respective fiber diameters of the fibers included in each measurement piece are found according to the aforementioned method. Fibers, whose fiber diameter is equal to or greater than the fiber diameter of the second fibers as found according to the aforementioned method, are determined as the second fibers, whereas fibers whose fiber diameter is equal to or less than the fiber diameter of the first fibers are determined as the first fibers. The number of second fibers included in the measurement piece is divided by the mass of the measurement piece. The average value found by repeating the measurement three times for each of the first layer and the second layer is found as the aforementioned ratio f2/f1.

For the first fibers and second fibers satisfying the aforementioned condition (2), it is possible to suitably use, for example, fusion-bondable fibers described in (1) above, and particularly fibers made of thermoplastic polymer materials. Particularly, it is possible to preferably use core-sheath conjugate fibers or side-by-side conjugate fibers including a combination of the aforementioned thermoplastic polymer materials. The first fibers and the second fibers may be the same type of fiber, or may be different types of fibers.

Crimped fibers are fibers whose crimped shape is helical, zig-zag shaped, U-shaped, or a combination thereof.

In cases of satisfying the aforementioned condition (3), from the viewpoint of increasing the degree of freedom of fibers between fusion-bonded points, it is preferable that the difference in the number of crimps, per 25 mm, between the first and second fibers is preferably 20 or greater, more preferably 30 or greater, on the premise that the number of crimps in the second fibers is larger than the number of crimps in the first fibers.

The number of crimps in the fibers is measured according to the method described in JIS L 1015. This measurement is performed for fibers taken out from ten discretionary sites in each of the first layer and the second layer of the first sheet; the average value of three fibers with the largest number of crimps is found as the number of crimps in the second fibers, and the average value of three fibers with the smallest number of crimps is found as the number of crimps in the first fibers.

When the content of the second fibers in the first layer is defined as f1 and the content of the second fibers in the second layer is defined as f2, the ratio (f2/f1) of f2 to f1 satisfying the aforementioned condition (3) is found on the basis of the respective number of crimps in fibers included in measurement pieces taken out from each of the first layer and the second layer, by determining whether the fibers are either first fibers or second fibers. First, a 4-mm square measurement piece is cut out from each of the first layer and the second layer of the first sheet, and the respective number of crimps in the fibers included in each measurement piece is found according to the aforementioned method. Fibers, whose number of crimps is equal to or greater than the number of crimps in the second fibers as found according to the aforementioned method, are determined as the second fibers, whereas fibers whose number of crimps is equal to or less than the number of crimps in the first fibers are determined as the first fibers. Other than determining the first fibers and second fibers in this way, the ratio f2/f1 is found as described in (2) above.

For the first fibers satisfying the aforementioned condition (3), it is possible to suitably use, for example, fusion-bondable fibers described in (1) above, and particularly fibers made of thermoplastic polymer materials. Particularly, it is possible to preferably use, for example, core-sheath conjugate fibers or side-by-side conjugate fibers including a combination of the aforementioned thermoplastic polymer materials.

Examples of the second fibers satisfying the aforementioned condition (3) include eccentric core-sheath conjugate fibers or side-by-side conjugate fibers including, as components thereof, two types of thermoplastic polymer materials having different shrinkage rates. Concrete examples thereof are described in JP H9-296325A and Japanese Patent No. 2759331. An example of a combination of polymer materials regarding "two types of thermoplastic polymer materials having different shrinkage rates" includes a combination of an ethylene-propylene random copolymer and polypropylene.

In cases of satisfying the aforementioned condition (4), from the viewpoint of increasing the degree of freedom of movement of fibers by reducing the degree of fusion-bonding between fibers and thereby reducing the number of fusion-bonded points between the fibers, it is preferable that the diameter ratio of the sheath component in the second fibers is preferably 99% or less, more preferably 91% or less, and preferably 60% or greater, more preferably 70% or greater, and preferably from 60 to 99%, more preferably from 70 to 91%, to the diameter ratio of the sheath component in the first fibers.

Figure 9:
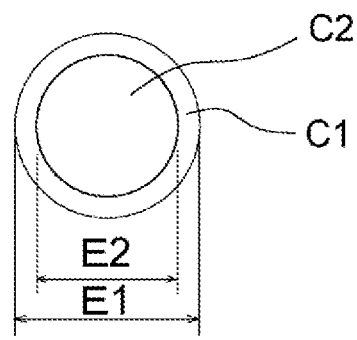
FIG. 9 is a diagram for illustrating a diameter ratio of a sheath component in a core-sheath conjugate fiber.

The diameter ratio AX of the sheath component in a core-sheath conjugate fiber is calculated according to the following equation, when the diameter of the sheath component C1 is defined as E1 and the diameter of the core component C2 is defined as E2. as illustrated in FIG. 9.

Diameter ratio AX of sheath component C1=Diameter E1 (μm) of sheath component of core-sheath conjugate fiber÷Diameter E2 (μm) of core component of core-sheath conjugate fiber.

Calculation of the diameter ratio AX of the sheath component is performed for fibers taken out from ten discretionary sites in each of the first layer and the second layer of the first sheet; the average value of three fibers with the smallest sheath-component diameter ratio AX is found as the sheath-component diameter ratio AX of the second fibers, and the average value of three fibers with the largest sheath-component diameter ratio AX is found as the sheath-component diameter ratio AX of the first fibers.

When the content of the second fibers in the first layer is defined as f1 and the content of the second fibers in the second layer is defined as f2, the ratio (f2/f1) of f2 to f1 satisfying the aforementioned condition (4) is found on the basis of the respective sheath-component diameter ratio of fibers included in measurement pieces taken out from each of the first layer and the second layer, by determining whether the fibers are either first fibers or second fibers. First, a 4-mm square measurement piece is cut out from each of the first layer and the second layer of the first sheet, and the respective sheath-component diameter ratio of the fibers included in each measurement piece is found according to the aforementioned method. Fibers, whose sheath-component diameter ratio is equal to or less than the sheath-component diameter ratio of the second fibers as found according to the aforementioned method, are determined as the second fibers, whereas fibers whose sheath-component diameter ratio is above the sheath-component diameter ratio of the first fibers are determined as the first fibers. Other than determining the first fibers and second fibers in this way, the ratio f2/f1 is found as described in (2) above.

For the first fibers and second fibers satisfying the aforementioned condition (4), it is possible to suitably use, for example, fusion-bondable fibers described in (1) above, and particularly fibers made of thermoplastic polymer materials. Examples particularly include core-sheath conjugate fibers including a combination of the aforementioned thermoplastic polymer materials. The first fibers and the second fibers may be the same type of fiber, or may be different types of fibers.

From the viewpoint of further facilitating deformation of the projections 4 formed on the skin-facing surface, the content of the second fibers in the second layer 1c is preferably at least 2 times, more preferably at least 4 times, the content of the second fibers in the first layer. This can be determined from the aforementioned ratio f2/f1.

From the viewpoint of further improving the degree of freedom of the movement of constituent fibers, the content of the second fibers in the second layer 1c is preferably 30% or greater, more preferably 45% or greater, and preferably 80% or less, more preferably 60% or less, and preferably from 30 to 80%, more preferably from 45 to 60%, to the entire mass of the second layer 1c.

The first layer 1b may include both the first fibers and second fibers, or may include only the first fibers. From the viewpoint of further facilitating deformation of the projections 4, the content of the second fibers in the first layer 1b is preferably 0% or greater, more preferably 5% or greater, and preferably 45% or less, more preferably 30% or less, and preferably from 0 to 45%, more preferably from 5 to 35%, to the entire mass of the first layer 1b.

Figure 10:
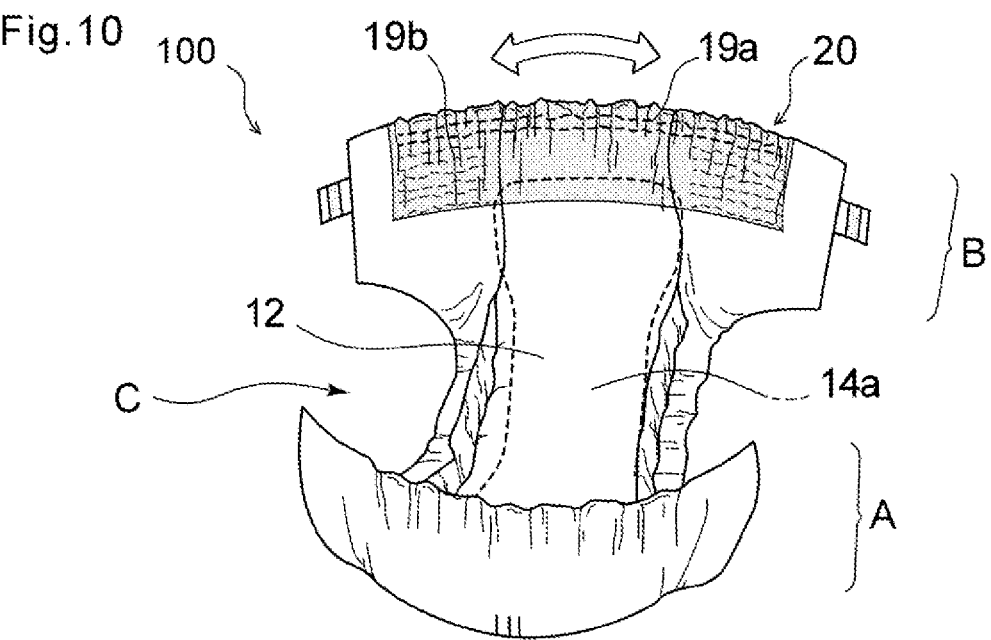
FIG. 10 is a perspective view in a state where elastic members in various parts of the diaper illustrated in FIG. 1 have contracted.

In at least a central portion, in the width direction Y, of the rear portion B, the diaper 100 includes a widthwise elasticized region 20 in which elastic members 19a, 19b extending in the width direction Y are provided. The widthwise elasticized region 20 is a region that is capable of expanding and contracting in the width direction Y along the waist peripheral edge portion, and as illustrated in FIGS. 2 and 10, includes: a waist-portion elastic region provided on the waist peripheral edge portion side; and hip-portion side elastic regions provided more toward the absorbent core 14a side than the waist-portion elastic region in the longitudinal direction X. The waist-portion elastic region includes waist-portion elastic members 19a that extend over the entire region of the elastic region in the width direction Y. The hip-portion side elastic regions each include hip-portion side elastic members 19b which are shorter in length than the waist-portion elastic members 19a, and are provided on both sides of the absorbent core 14a in the width direction Y. Hereinbelow, the waist-portion elastic members 19a and the hip-portion side elastic members 19b may also be collectively referred to as elastic members 19.

As illustrated in FIGS. 2 and 10, the projecting-and-depressed sheet 10 in the diaper 100 is arranged so as to extend from the rear portion B to the front portion A via the crotch portion C, and overlaps the widthwise elasticized region 20 in the rear portion B. In cases where the projecting-and-depressed sheet 10 partially overlaps the widthwise elasticized region 20, which is capable of expanding and contracting in the width direction Y, the movable range or maximum movable direction of the projections 4 becomes different between the section overlapping the widthwise elasticized region 20 and non-overlapping sections. More specifically, in the section of the projecting-and-depressed sheet 10 overlapping the widthwise elasticized region 20, the projections 4 expand and contract in the width direction Y following the elastic members 19 that expand and contract in the width direction Y. Thus, in the section of the projecting-and-depressed sheet 10 overlapping the widthwise elasticized region 20, the movable range, in the width direction Y, of the respective apexes of the projections 4 is increased, thereby being able to offer a smoother feel and better texture. As described above, the movable range or maximum movable direction of the projections 4 may become different due to the expansion/contraction, in one direction, of the projections 4 overlapping the elasticized region. The "maximum movable direction of the projections 4" refers to a direction in which the respective apexes of the projections can move the most following the movement of an object in contact.

The "maximum movable direction of the projections" is the tensile direction in which the tensile distance becomes the greatest according to the aforementioned {Method for Measuring Movable Range of Apex of Projection}.

As illustrated in FIG. 1, in the diaper 100, the topsheet 12 is arranged so as to extend from the rear portion B to the front portion A via the crotch portion C. As described above, the topsheet 12 is the projecting-and-depressed sheet 10.

From the viewpoint of allowing the projections of the projecting-and-depressed sheet to follow the wearer's movement around the hip more easily and reducing friction between the projecting-and-depressed sheet and the hip, it is preferable that the movable range, in the longitudinal direction X, of the apex of the projections 4 is longer in the projecting-and-depressed sheet 10 in the rear portion B than in the crotch portion C. From the viewpoint of achieving the aforementioned effects more reliably, it is preferable that the movable range Fb, in the longitudinal direction X, of the apex of the projections 4 in the rear portion B is preferably 1.2 times or greater, more preferably 1.5 times or greater, and preferably 5 times or less, more preferably 3 times or less, and preferably from 1.2 to 5 times, more preferably from 1.5 to 3 times, to the movable range Fc of the apex of the projections 4 in the crotch portion C.

From the viewpoint of improving texture, the cool contact sensation q-max of the projecting-and-depressed sheet 10 is preferably 0.2 kW/m$^2$ or greater, and preferably 0.7 kW/m$^2$ or less, more preferably 0.6 kW/m$^2$ or less, even more preferably 0.5 kW/m$^2$ or less. "Cool contact sensation" is the skin sensation whereby an object feels cool when the skin touches the object. This cool contact sensation differs depending on the amount of heat transferred from the skin to an object when the skin touches the object; the greater the heat transfer amount, the cooler the object feels. The cool contact sensation q-max corresponds to the maximum value of the amount of heat transferred from the skin to an object; the cooler an object feels when touched, the greater the value of the cool contact sensation q-max, whereas the warmer the object feels, the smaller the value. Also, the cooler an object feels when touched, the more likely it is to feel uncomfortable.

The cool contact sensation q-max is measured according to the following method.

{Method for Measuring Cool Contact Sensation Q-max}

Cool contact sensation q-max is the maximum value of heat flow found by: first accumulating heat in a temperature sensor-equipped heated plate, such as a metal plate, to set the temperature of the heated plate higher than a measurement object; bringing the heated plate into contact with the surface of the measurement object; and finding the maximum value of heat flow when the heat accumulated in the heated plate transfers, immediately after contact, to the lower-temperature-side measurement object.

Measurement of cool contact sensation q-max can be performed according to the following method using a commercially available measurement device (precise rapid thermophysical property measurement device KES-F7 Thermo Labo II from Kato Tech Co., Ltd.). First, a test piece that is 10 cm long in the longitudinal direction and 7 cm long in the width direction is cut out from a region of the projecting-and-depressed sheet where a plurality of projections are formed. The test piece is allowed to stand in an environment at room temperature (23° C.) at a relative humidity of 50% for 24 hours. Next, in this environment, the test piece is placed on a measurement stage with the skin-facing surface facing up, and the test piece is fixed to the measurement stage with a double-faced paper tape. The double-faced paper tape is attached to the test piece's non-skin-facing surface respectively at positions 1 cm inward in the longitudinal direction from both ends in the longitudinal direction, to suppress creases from forming in the test piece. For the measurement stage, it is possible to use a thermostat using a gas or liquid as the heating medium. Next, the cool contact sensation q-max of the measurement object is measured using KES-F7 Thermo Labo II from Kato Tech Co., Ltd. according to the measurement manual from Kato Tech Co., Ltd. More specifically, a pure copper plate having an area of 9.0 cm$^2$ and mass of 9.8 g is used as the aforementioned heated plate to be brought into contact with the measurement object. The copper plate is set to an initial temperature of 33° C. (which is 10° C. higher than the surface temperature of the measurement object). The copper plate is brought into contact with the skin-facing surface of the projecting-and-depressed sheet, with the contact pressure of the copper plate against the measurement object being set to 1 kPa, and the maximum value of heat flow is measured, considering that the heat flow value at the instant of contact is zero. This measurement is performed five times for the measurement object surface, and the average value of the measurement values is found as the cool contact sensation q-max of the measurement object surface.

As described above, by making the projecting-and-depressed sheet 10 contact the user's skin etc. and applying tactile stimulation, the projecting-and-depressed sheet 10 is capable of increasing the amount of oxytocin. The amount of oxytocin can be measured according to a method including the following steps (A) to (C):

(A) a step of bringing a test sheet to be evaluated into contact with the skin or hair of an animal and applying tactile stimulation to the animal;

(B) a step of sampling a biological sample from the animal after applying the tactile stimulation; and (C) a step of measuring the amount of oxytocin in the biological sample.

The method including the aforementioned steps (A) to (C) is also called an oxytocin amount measurement method.

"Animals" as referred to in the oxytocin amount measurement method are mammals, including human beings, producing oxytocin, with examples including human beings and non-human animals such as chimpanzees, monkeys, dogs, bovines, swine, rabbits, guinea pigs, rats, and mice (Yamashita and Kitano, Mol. Phylogenet. Evol., 2013, 2, 520-528).

In step (A), the skin-facing surface of the projecting-and-depressed sheet—i.e., the surface having the projections 4 formed thereon—is brought into contact with the skin or hair of an animal, to apply tactile stimulation to the animal. The "skin or hair of an animal" is not particularly limited so long as it is the skin or hair of an animal. "Skin" may include, for example: a part of the hand, such as the finger, palm, or the back of the hand; upper arm; elbow; lower arm; a part of the foot, such as the toes or the sole; thigh; back; chest; shoulder; neck; head; and buttock. "Skin", when classified according to the presence/absence of hair roots, can be classified into hairy parts having hair roots and hairless parts lacking hair roots; the "skin" can either be a hairy part, hairless part, or both. Examples of hairless parts include the palm and the sole; mucosal parts, however, are excluded. "Hair" of an animal include the hair on one's head or body hair.

"Tactile stimulation" is stimulation perceived by contact between the projecting-and-depressed sheet and the skin or hair. In step (A), tactile stimulation may be applied in a still state without movement while keeping the projecting-and-depressed sheet in contact with the skin or hair, or tactile stimulation may be applied in a moving state involving movement while keeping the projecting-and-depressed sheet in contact with the skin or hair. An example of a mode for applying tactile stimulation in a moving state includes stroking the projecting-and-depressed sheet with the skin or hair in the planar direction. In cases where the animal is a human being, an example of this mode includes stroking the projecting-and-depressed sheet back and forth in the sheet's longitudinal direction with the palm while keeping the palm in contact with the skin-facing surface of the projecting-and-depressed sheet.

Contact between the projecting-and-depressed sheet and the skin or hair may be made voluntarily by the animal, or may be forced.

In step (A), tactile stimulation may be applied continuously or intermittently. An example of a mode wherein tactile stimulation is applied intermittently includes a mode of repeating a cycle including: a step of applying tactile stimulation by bringing a contact portion and a test sheet into contact with one another; and a step of keeping the contact portion in a resting state where it contacts nothing. Stated differently, the mode may alternately repeat application of tactile stimulation and a resting state.

The time over which the tactile stimulation is applied is not particularly limited, and may preferably be 30 seconds or longer, more preferably 45 seconds or longer, even more preferably 60 seconds or longer, and preferably 600 seconds or shorter, more preferably 450 seconds or shorter, even more preferably 300 seconds or shorter, and preferably from 30 to 600 seconds, more preferably from 45 to 450 seconds, even more preferably from 60 to 300 seconds. In cases of applying the tactile stimulation intermittently, the time over which the tactile stimulation is applied is preferably the total time over which the contact portion and the test sheet are placed in contact with one another in each step for applying the tactile stimulation.

In step (A), a projecting-and-depressed sheet taken out from an absorbent article, or a projecting-and-depressed sheet still incorporated in an absorbent article, is brought into contact with the skin or hair, to apply tactile stimulation. Also, tactile stimulation may be applied in a state where the projecting-and-depressed sheet or the absorbent article can or cannot be seen. An example of a state where the sheet/article cannot be seen includes a mode wherein the projecting-and-depressed sheet is placed in a blinded box having an opening through which the hand can be passed in and out, and the hand inserted through the opening touches the sheet in this state. In cases where the animal is a human being, when applying tactile stimulation, it is preferable to tell the evaluator that, for example, a sheet material used in a disposable diaper is being evaluated, from the viewpoint of accurately judging/evaluating the effect of increasing the amount of oxytocin.

In step (B), a biological sample is sampled from the animal to which the tactile stimulation has been applied in step (A). The timing for sampling the biological sample from the animal is after application of the tactile stimulation, and is preferably within 60 minutes after applying the tactile stimulation, but sampling may be performed during application of the tactile stimulation after applying the tactile stimulation for a predetermined duration. Alternatively, the sampling timing may be after the lapse of a predetermined time from when the contact portion has been placed in a resting state after application of the tactile stimulation. From the viewpoint of accurately monitoring the effect of increasing the amount of oxytocin after application of tactile stimulation, it is preferable that, in step (B), the biological sample is sampled from the animal preferably within 50 minutes, more preferably within 40 minutes, after applying the tactile stimulation. In cases where the time is measured from the point when application of tactile stimulation was started, with consideration given to the time for applying the tactile stimulation continuously or intermittently, it is preferable that sampling of the biological sample from the animal is performed preferably within 65 minutes, more preferably within 55 minutes, even more preferably within 45 minutes, from the point when application was started.

Concrete examples of biological samples sampled in step (B) include blood, urine, saliva, lymph fluid, etc. Blood plasma, blood serum, blood cells (erythrocytes or leukocytes), etc., may be fractionated from blood according to a known method, and one of the above may be used as the biological sample. Preferably, the sampled biological sample is immediately cryopreserved with dry ice etc.

In cases of sampling saliva as the biological sample, the sampling method is not particularly limited, with examples including the spitting method, cotton method, etc. For example, sampling may be performed by first rinsing the oral cavity with water and then making the testee spit out all his/her saliva into a predetermined container.

In step (C), the amount of oxytocin in the biological sample sampled in step (B) is measured. The method for measuring the amount of oxytocin is not particularly limited, with usable examples including liquid chromatography (HPLC), liquid chromatography-mass spectrometry (LC-MS), liquid chromatography-tandem mass spectrometry (LC-MS/MS), gas chromatography-mass spectrometry (GC-MS), and immunological methods such as enzyme-linked immunosorbent assay (ELISA).

Measurement conditions therefor are known in the art, and quantity can be determined easily according to ordinary methods. ELISA can be performed, for example, by using an Oxytocin ELISA kit (from Enzo).

A method including the following step (D), in addition to the steps (A) to (C), can determine whether or not application of tactile stimulation has a function of increasing the amount of oxytocin in the biological sample.

(D) A step of comparing the measured amount of oxytocin with an amount of oxytocin in a biological sample sampled from an animal under a condition not affected by tactile stimulation.

In step (D), the amount of oxytocin measured in step (C) is compared with an amount of oxytocin in a biological sample sampled from an animal under a condition not affected by tactile stimulation. In this way, it is possible to verify whether or not tactile stimulation by the projecting-and-depressed sheet can increase the amount of oxytocin compared to the amount of oxytocin in a biological sample sampled from an animal under a condition not affected by tactile stimulation. The effect of increasing the amount of oxytocin by tactile stimulation is also called "oxytocin amount increasing effect". The amount of oxytocin in a biological sample sampled from an animal after application of tactile stimulation is also called "tactilely-stimulated oxytocin amount", and the amount of oxytocin in a biological sample sampled from an animal under a condition not affected by tactile stimulation is also called "steady-state oxytocin amount". The tactilely-stimulated oxytocin amount and the steady-state oxytocin amount may be compared by same-individual comparison, wherein a biological sample after application of tactile stimulation is compared with a biological sample not affected by tactile stimulation, both samples being sampled from the same individual animal. In this case, examples of the "biological sample sampled from an animal under a condition not affected by tactile stimulation" include samples obtained at a timing before application of tactile stimulation, or at a timing after a given time has lapsed from application of tactile stimulation and when the change in the amount of oxytocin caused by the tactile stimulation has subsided.

Alternatively, the comparison between the tactilely-stimulated oxytocin amount and the steady-state oxytocin amount in step (D) may be an individual-group comparison, wherein biological samples obtained from a group of individuals subjected to tactile stimulation are compared with biological samples obtained from another group of individuals not subjected to tactile stimulation. It is preferable that both individual groups have the same attributes, wherein factors, such as type, age, gender, and birthing/parenting experience or lack thereof, match one another. In cases of performing individual-group comparison, the expression "under a condition not affected by tactile stimulation" refers to "another group of individuals not subjected to tactile stimulation".

In step (D), the presence/absence of the oxytocin amount increasing effect may be determined, for example, based on the rate of change (%) of the tactilely-stimulated oxytocin amount to the steady-state oxytocin amount, or based on the difference between the steady-state oxytocin amount and the tactilely-stimulated oxytocin amount. In cases of comparison based on the rate of change (%), it is determined that the test sheet has the oxytocin amount increasing effect if the rate of change of the tactilely-stimulated oxytocin amount to the steady-state oxytocin amount has increased by a predetermined value or greater. For example, in cases of performing same-individual comparison, it is determined that the projecting-and-depressed sheet has the oxytocin amount increasing effect if the ratio of the tactilely-stimulated oxytocin amount to the steady-state oxytocin amount—i.e., the rate of change in the amount of oxytocin—is preferably 10% or higher, more preferably 30% or higher. In cases of performing individual-group comparison, it is determined that the test sheet has the oxytocin amount increasing effect if the amount of oxytocin of biological samples sampled from a group of individuals subjected to tactile stimulation is preferably 10% or higher, more preferably 30% or higher, than the amount of oxytocin of biological samples sampled from another group of individuals not subjected to tactile stimulation.

In cases of determining the presence/absence of the oxytocin amount increasing effect on the basis of the difference between the steady-state oxytocin amount and the tactilely-stimulated oxytocin amount, the projecting-and-depressed sheet may be determined as having the oxytocin amount increasing effect if the difference between the steady-state oxytocin amount and the tactilely-stimulated oxytocin amount, which is found on the premise that the tactilely-stimulated oxytocin amount is greater than the steady-state oxytocin amount, is equal to or greater than a predetermined value. Whether or not the difference is equal to or greater than a predetermined value can be determined, for example, on the basis of the ratio between the steady-state oxytocin amount and the difference between the steady-state oxytocin amount and the tactilely-stimulated oxytocin amount. This ratio may simply be called "ratio of difference". When the steady-state oxytocin amount is defined as Ha and the tactilely-stimulated oxytocin amount is defined as Hb, the ratio of difference H is expressed by the following equation.

$$\text{Ratio of difference } H(\%)=[(Hb-Ha)/Ha] \times 100$$

In step (D), it is determined that the test sheet has the oxytocin amount increasing effect if the ratio of difference H is equal to or higher than a predetermined value—for example, has a high value of preferably 10% or greater, preferably 30% or greater. Further, in cases where, in step (D), when the amount of oxytocin in biological samples sampled from a group of individuals subjected to tactile stimulation is defined as the tactilely-stimulated oxytocin amount Hb and the amount of oxytocin in biological samples sampled from another group of individuals not subjected to tactile stimulation is defined as the steady-state oxytocin amount Ha, it is determined that the test sheet has the oxytocin amount increasing effect if the ratio of difference H has a high value of preferably 10% or greater, preferably 30% or greater.

Alternatively, whether or not the difference between the steady-state oxytocin amount and the tactilely-stimulated oxytocin amount is equal to or greater than a predetermined value may be determined based on the absolute amount of the difference.

According to the above methods, it is possible to verify whether or not tactile stimulation by the projecting-and-depressed sheet increases the amount of oxytocin.

The first sheet 1 and the second sheet 2 forming the composite sheet are each made of a sheet material. For the sheet material, it is possible to use, for example, a fiber sheet, such as a nonwoven fabric, a woven fabric, or a knitted fabric, or a film. From the viewpoint of texture etc., it is preferable to use a fiber sheet, more preferably a nonwoven fabric. The sheet materials constituting the first sheet 1 and the second sheet 2 may be of the same type, or may be different from one another.

In cases of using a nonwoven fabric as the sheet material constituting the first sheet 1 and the second sheet 2, examples of the nonwoven fabric include air-through nonwoven fabric, spunbond nonwoven fabric, spun-laced nonwoven fabric, melt-blown nonwoven fabric, resin-bonded nonwoven fabric, and needle-punched nonwoven fabric. It is also possible to use a laminate made by using two or more types of the aforementioned nonwoven fabrics in combination, or a laminate made by using the aforementioned nonwoven fabric(s) and a film in combination. Among the above, it is preferable to use an air-through nonwoven fabric or a spunbond nonwoven fabric.

The basis weight of the nonwoven fabric used as the sheet material constituting the first sheet 1 and the second sheet 2 is preferably 10 $g/m^2$ or greater, more preferably 15 $g/m^2$ or greater, and preferably 40 $g/m^2$ or less, more preferably 35 $g/m^2$ or less, and preferably from 10 to 40 $g/m^2$, more preferably from 15 to 35 $g/m^2$.

In cases where the first sheet 1 and the second sheet 2 are joined together by fusion-bonding as described below, it is preferable that the fibers constituting the nonwoven fabric include a thermoplastic resin given as examples of first fibers and second fibers above. One type of resin may be used singly, or two or more types may be used as a blend. The fibers may be used in the form of core-sheath or side-by-side conjugate fibers.

As illustrated in FIG. 4, in the projecting-and-depressed sheet 10, the joined portions 30 joining the first sheet 1 and the second sheet 2 form: a plurality of first oblique joined portion rows S1, each including a plurality of joined portions 30 lined up along a first direction D1 oblique to both the longitudinal direction X and the width direction Y; and a plurality of second oblique joined portion rows S2, each including a plurality of joined portions 30 lined up along a second direction D2 that intersects with the first direction D1 and is oblique to both the longitudinal direction X and the width direction Y.

At respective intersecting portions between the first oblique joined portion rows S1 and the second oblique joined portion rows S2, long joined portions 31, each having a long shape in the longitudinal direction X, are formed as the joined portions 30. In the first oblique joined portion rows S1 and the second oblique joined portion rows S2 of the present embodiment, intersecting portions are provided at given intervals in both the first direction D1 and the second direction D2, and a long joined portion 31 is provided in each intersecting portion. Preferably, the first direction D1 and the second direction D2 has line symmetry with respect to a straight line parallel to the center line CL in the longitudinal direction.

Further, in the projecting-and-depressed sheet 10, laterally-long projections 42, each having a long shape in the width direction Y, are formed as the projections 4 in a dispersed state in the longitudinal direction X and the width direction Y.

The laterally-long projections 42 are arranged in a staggered pattern. More specifically, as illustrated in FIG. 4, the laterally-long projections 42 are arranged so as to include: longitudinal-direction projection rows R3, each including a plurality of the laterally-long projections 42 arranged in a line along the longitudinal direction X at given intervals; width-direction projection rows R4, each including a plurality of the laterally-long projections 42 arranged in a line along the width direction Y at given intervals; first-direction projection rows R5, each including a plurality of the laterally-long projections 42 arranged in a line along the first direction D1 at given intervals; and second-direction projection rows R6, each including a plurality of the laterally-long projections 42 arranged in a line along the second direction D2 at given intervals.

In the longitudinal-direction projection rows R3 adjacent to one another in the width direction Y, the laterally-long projections 42 are arranged at positions misaligned from one another by half-pitch in the longitudinal direction X. In the width-direction projection rows R4 adjacent to one another in the longitudinal direction X, the laterally-long projections 42 are arranged at positions misaligned from one another by half-pitch in the width direction Y.

Short joined portions 32, whose length in the longitudinal direction X is shorter than that of the long joined portion 31, are provided between adjacent long joined portions 31 in each of the first oblique joined portion rows S1 and second oblique joined portion rows S2.

As illustrated in FIG. 5, the short joined portions 32 in the present embodiment form: a plurality of longitudinal-direction short joined portion rows S4, each including a plurality of the short joined portions 32 arranged in a line along the longitudinal direction X at given intervals; and a plurality of width-direction short joined portion rows S5, each including a plurality of the short joined portions 32 arranged in a line along the width direction Y at given intervals.

The longitudinal-direction short joined portion rows S4 adjacent to one another in the width direction Y are located between longitudinal-direction long joined portion rows S3 adjacent to one another in the width direction Y.

As illustrated in FIG. 4, each laterally-long projection 42 in the present embodiment is formed in a state surrounded by two first oblique joined portion rows S1, S1 and two second oblique joined portion rows S2, S2. More specifically, each laterally-long projection 42 is formed within a region surrounded by: four long joined portions 31 respectively located at intersecting portions between the first oblique joined portion rows S1 and the second oblique joined portion rows S2; and four or more short joined portions 32—more specifically, eight short joined portions 32—located between the four long joined portions 31.

Further, as illustrated in FIG. 5, as regards each of the laterally-long projections 42 in the present embodiment, one long joined portion 31, which has a long shape in the longitudinal direction X, is formed between the laterally-long projections 42, 42 adjacent to one another in the width direction Y.

More specifically, as illustrated in FIG. 4, in the projecting-and-depressed sheet 10, a plurality of width-direction composite rows R9 are formed in the longitudinal direction X, each width-direction composite row R9 including the laterally-long projections 42 and the long joined portions 31 arranged alternately in the width direction Y. In the width-direction composite rows R9 adjacent to one another in the longitudinal direction X, the laterally-long projections 42 and the long joined portions 31 are arranged at positions misaligned from one another by half-pitch in the width direction Y.

At each joined portion 30, the constituent resin of the constituent fibers in one or both the first sheet 1 and the second sheet 2 is in a molten/solidified state. Further, at each joined portion 30, the first sheet 1 and the second sheet 2 are highly densified compared to other sections (sections other than the joined portions). Stated differently, the joined portions 30 in the projecting-and-depressed sheet 10 are preferably fusion-bonded portions formed by integrally heating and pressurizing the first sheet 1 and the second sheet 2, wherein both sheets are bonded with one another by melting of the constituent resin of the constituent fibers in one or both the sheets and the subsequent solidification. At each joined portion 30, it is preferable that both the first sheet 1 and the second sheet 2 are molten/solidified. Alternatively, at the joined portion 30, the first sheet 1 and the second sheet 2 may be joined together by a joining means other than fusion-bonding, such as an adhesive, e.g., a hot-melt adhesive.

From the viewpoint of improving texture, it is preferable that the projections of the projecting-and-depressed sheet 10 have the following configuration.

It is preferable that the ratio (L1/L2) of the length L1 (see FIG. 6(b)) of the laterally-long projection 42 in the width direction Y to the length L2 (see FIG. 6(a)) in the longitudinal direction X is preferably 1.1 or greater, more preferably 1.5 or greater, and preferably 6.0 or less, more preferably 4.0 or less, and preferably from 1.1 to 6.0, more preferably from 1.5 to 4.0. The length L1 of the laterally-long projection 42 in the width direction Y is preferably 3 mm or greater, more preferably 5 mm or greater, and preferably 30 mm or less, more preferably 15 mm or less, and preferably from 3 to 30 mm, more preferably from 5 to 15 mm. The length L2 of the laterally-long projection 42 in the longitudinal direction X is the aforementioned length L2, in the longitudinal direction X, of the bottom portion 41 of the projection 4. The length L1 in the width direction Y is measured by considering the width direction Y as the "given direction" in the aforementioned {Measurement of Length of Bottom Portion of Projection}. More specifically, the distance between the start point and the endpoint of a line forming the projection's outline within the cut cross-section along the projecting-and-depressed sheet's width direction Y is measured (see FIG. 6(b)). The distance between the start point and the endpoint is measured at a position, in the projection's thickness direction, at which the length between the start point and the endpoint becomes the longest in the width direction Y. The distance is measured for at least five projections, and the average value is found as the length L1 of the projection in the width direction Y.

The length L1, in the width direction Y, of the laterally-long projection 42 is the distance between the long joined portions 31 in the width-direction composite row R9. The length L2, in the longitudinal direction X, of the laterally-long projection 42 is the same as the distance between the long joined portions 31 in the longitudinal-direction long joined portion row S3.

The height H1 (see FIG. 6(b)) of the laterally-long projection 42 is preferably 0.5 mm or greater, more preferably 1.0 mm or greater, and preferably 5.0 mm or less, more preferably 4.0 mm or less, and preferably from 0.5 to 5.0 mm, more preferably from 1.0 to 4.0 mm. In relation to the projection 4 of the composite sheet, "height" is defined as the distance from the lower surface of the second sheet 2 to the upper surface of the first sheet 1, as illustrated in FIG. 6(b). The height is the value obtained by observing the cross section of each projection with a digital microscope (from Keyence) and measuring the shortest distance between the lower surface of the second sheet 2 and the apex of the projection.

In the projecting-and-depressed sheet 10 of the present embodiment, as illustrated in FIG. 5, a plurality of the longitudinal-direction joined portion rows S3, S4—each including the joined portions 30 arranged in a line along the longitudinal direction X with intervals therebetween—are formed in the width direction Y, and a portion, or all, of the joined portions 30 in the longitudinal-direction joined portion rows adjacent to one another in the width direction Y overlap(s) one another in the longitudinal direction X, or the positions of the joined portions' ends in the longitudinal direction X match one another.

The projecting-and-depressed sheet 10 having the aforementioned configuration can be manufactured according to a method similar to the method described in JP 2015-112343A. That is, a continuous first sheet 1 is supplied between a first roller and a second roller whose respective circumferential surfaces have intermeshing shapes, thereby deforming the first sheet 1 into a projecting-and-depressed shape, and then, the first sheet 1 is moved away from the intermeshing section while keeping the sheet along the circumferential surface portion of the first roller. Then, a second sheet 2 is supplied onto the first sheet 1, and the two sheets 1, 2 are partially joined together by being sandwiched and pressurized, while being heated, between the projections of the first roller and a heat roller. At this time, the projecting-and-depressed shapes of the first roller and the second roller, as well as the patterns of the joined portions formed by the first roller and the heat roller, are made different between the central portion and the lateral side portions of the first sheet. At the time of feeding the first sheet 1 into the intermeshing section between the first roller and the second roller to deform the sheet into a projecting-and-depressed shape, it is preferable to suck the first sheet toward the inner side of the roller and promote deformation of the first sheet 1 into the projecting-and-depressed shape.

Figure 11:
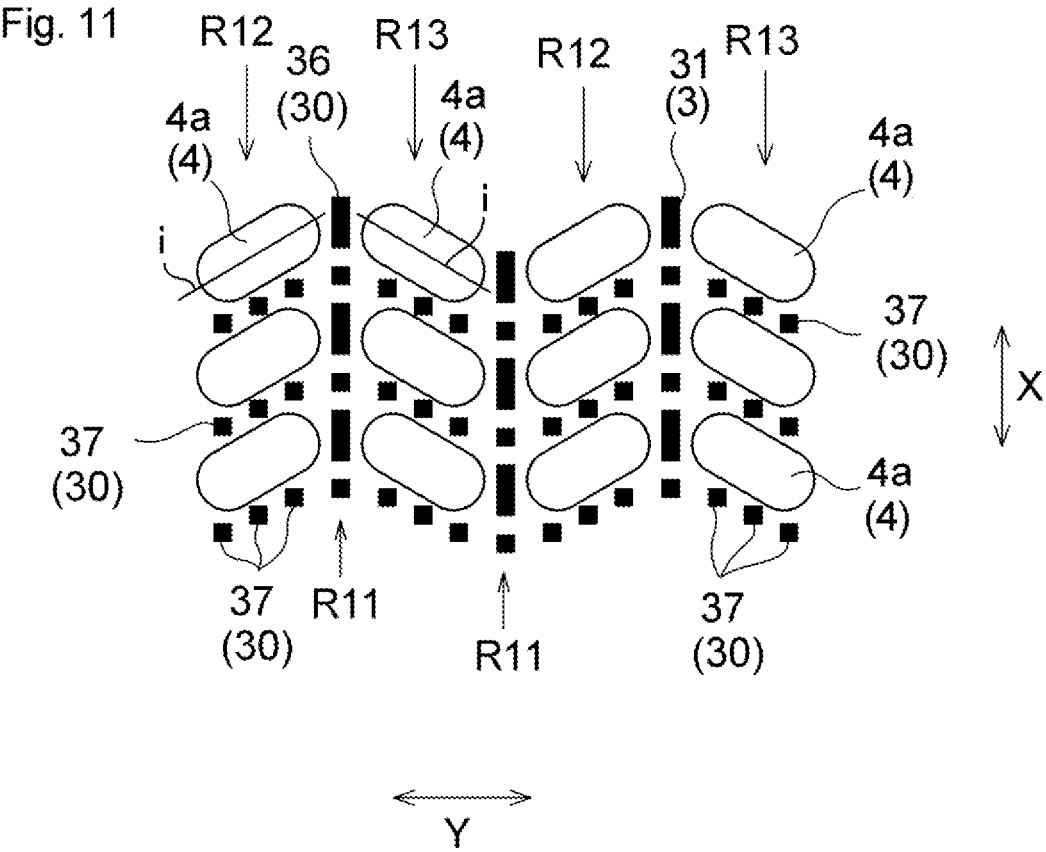
FIG. 11 is a diagram corresponding to FIG. 4, illustrating yet another embodiment of the present invention.
Figure 12:
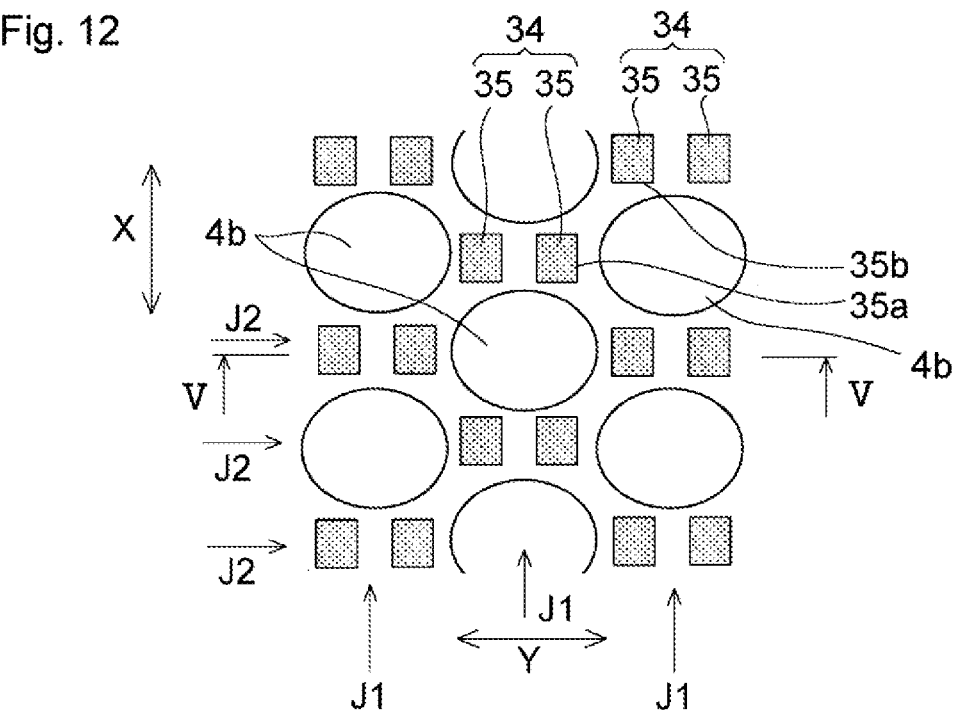
FIG. 12 is a diagram corresponding to FIG. 4, illustrating yet another embodiment of the present invention.

FIGS. 11 and 12 illustrate other embodiments of projecting-and-depressed sheets according to the present invention. The explanation on the first embodiment applies as appropriate to the following second and third embodiments, except that the patterns for forming the depressions and projections are different. In the second and third embodiments, constituent features that are the same as those in the first embodiment are accompanied by the same reference signs and explanation thereon is omitted. The explanation on the first embodiment applies as appropriate to constituent features that are not described in particular.

In the projection 4 in the foregoing first embodiment, the line i, which connects two points arranged at positions that provide the projection 4 with the longest length, is parallel to the width direction Y, as illustrated in FIG. 5. The line i is also called the "longest line i". In the second embodiment, the longest line i of each projection 4 does not have to be parallel to the width direction Y, as illustrated in FIG. 11. Each projection 4a illustrated in FIG. 11 has a shape that is long in one direction in a planar view, and its longest line is oblique to both the longitudinal direction X and the width direction Y. With this configuration, the maximum movable direction of the apex of the projection 4a is in a slanting direction with respect to the longitudinal direction X, and thus, the projection can easily move in the slanting direction. The projection 4a whose longest line i is oblique to the longitudinal direction X and to the width direction Y is also called an "oblique projection 4a".

FIG. 11 illustrates two types of longitudinal-direction oblique projection rows R12, R13, each including a plurality of the oblique projections 4a formed along the longitudinal direction X. There are a plurality of the two types of longitudinal-direction oblique projection rows R12, R13. A composite joined portion row R11, wherein joined portions 36 having a long shape in the longitudinal direction X and square-shaped joined portions 37 are arranged alternately along the longitudinal direction X, is arranged between two projection rows R12, R13. The two types of longitudinal-direction oblique projection rows R12, R13 are arranged with line symmetry with respect to the composite joined portion row R11. With this configuration, the tactile feeling along the longitudinal direction X becomes smoother and texture is further improved between the longitudinal-direction oblique projection rows R12, R13 arranged with line symmetry. As described above, it is preferable to arrange two oblique projection rows, each including a plurality of oblique projections, so as to have line symmetry with one another.

As illustrated in FIG. 5, the projection 4 in the foregoing first embodiment is a laterally-long projection 42 having a shape that is long in the width direction Y in a planar view. In contrast, the projection 4b of the third embodiment has an aspect ratio (height/width ratio) close to 1.0, when the longitudinal direction X is defined as height and the width direction Y is defined as width, and a plurality of such projections 4b are arranged in a staggered pattern, as illustrated in FIG. 12. The projecting-and-depressed sheet 10c of this embodiment includes: a plurality of longitudinal-direction composite rows J1, in each of which the projections 4b and joined portion pairs 34—each consisting of a pair of joined portions 35, 35 closely arranged with a given interval therebetween—are alternately arranged at given intervals along the longitudinal direction X; and a plurality of width-direction composite rows J2, in each of which the projections 4b and the joined portion pairs 34 are alternately arranged at given intervals along the width direction Y.

The present invention has been described above according to preferred embodiments thereof, but the present invention is not limited to the foregoing embodiments and may be modified as appropriate.

For example, in the foregoing embodiments, the projecting-and-depressed sheet 10 is used for the topsheet 12, but the projecting-and-depressed sheet 10 may be used by being arranged on the outer surface of the diaper. In the foregoing embodiments, the projecting-and-depressed sheet is used as the topsheet, but it may be used, for example, for other constituent members, such as an outer cover. Even when the projecting-and-depressed sheet is used, for example, as an outer cover, the sheet will come into contact with the skin of a user, such as a wearer or a parent/guardian, and can thus achieve an effect of offering a pleasant sensation to the user.

The shapes and arrangements of the joined portions 31, 32 in the depressions 3, as well as other joined portions, can be determined as appropriate. Other than rectangular and square as illustrated in FIG. 3, each of the joined portions may have discretionary shapes, such as circular, elliptic, oval, triangular, quadrangular, pentagonal, hexagonal, star-shaped, or heart-shaped.

The absorbent article of the present invention may be an underpants-type (pull-on-type) disposable diaper instead of an open-type disposable diaper, or may be a pull-on sanitary napkin, a normal non-pull-on sanitary napkin, an incontinence pad, a pantiliner, or the like.

In relation to the foregoing embodiments, the present invention also discloses the following absorbent articles.

{1}
An absorbent article comprising a projecting-and-depressed sheet as a constituent member, the absorbent article having a longitudinal direction that corresponds to a front-rear direction of a wearer and a width direction that is orthogonal to the longitudinal direction, wherein:
 the projecting-and-depressed sheet has a plurality of depressions and projections on a skin-facing surface to be brought into contact with the wearer's skin;
 in a given direction, a movable range of an apex of the projection of the projecting-and-depressed sheet is 30% or greater to a length of a bottom portion of the projection;
 on the skin-facing surface of the projecting-and-depressed sheet, a mean friction coefficient MIU in the given direction is 0.3 or less, and a difference in friction coefficient between a forward path and a return path when moved back and forth along the given direction is less than 0.1; and
 the projecting-and-depressed sheet has a work of compression of 2.0 mN·cm/cm² or greater and a compression recovery rate of 40% or greater.

{2}
The absorbent article as set forth in clause {1}, wherein the movable range of the apex of the projection is from 30 to 100% to the length of the bottom portion of the projection.

{3}
The absorbent article as set forth in clause {1}, wherein the movable range of the apex of the projection is from 35 to 100% to the length of the bottom portion of the projection.

{4}
The absorbent article as set forth in clause {1}, wherein the movable range of the apex of the projection is from 45 to 85% to the length of the bottom portion of the projection.

{5}
The absorbent article as set forth in any one of clauses {1} to {4}, wherein the mean friction coefficient MIU is from 0.1 to 0.3.

{6}
The absorbent article as set forth in any one of clauses {1} to {4}, wherein the mean friction coefficient MIU is from 0.1 to 0.27.

{7}
The absorbent article as set forth in any one of clauses {1} to {4}, wherein the mean friction coefficient MIU is from 0.1 to 0.24.

{8}
The absorbent article as set forth in any one of clauses {1} to {7}, wherein the difference in friction coefficient is 0.001 or greater to less than 0.1.

{9}
The absorbent article as set forth in any one of clauses {1} to {7}, wherein the difference in friction coefficient is from 0.001 to 0.07.

{10}
The absorbent article as set forth in any one of clauses {1} to {7}, wherein the difference in friction coefficient is from 0.001 to 0.04.

{11}
The absorbent article as set forth in any one of clauses {1} to {10}, wherein the work of compression is from 2.0 to 20 mN·cm/cm².

{12}
The absorbent article as set forth in any one of clauses {1} to {10}, wherein the work of compression is from 2.5 to 20 mN·cm/cm².

{13}
The absorbent article as set forth in any one of clauses {1} to {10}, wherein the work of compression is from 3.5 to 20 mN·cm/cm².

{14}
The absorbent article as set forth in any one of clauses {1} to {13}, wherein the compression recovery rate is from 40 to 85%.

{15}
The absorbent article as set forth in any one of clauses {1} to {13}, wherein the compression recovery rate is from 46 to 85%.

{16}
The absorbent article as set forth in any one of clauses {1} to {13}, wherein the compression recovery rate is from 52 to 85%.

{17}
The absorbent article as set forth in clause {1}, the absorbent article comprising the projecting-and-depressed sheet as a constituent member and having the longitudinal direction that corresponds to the front-rear direction of the wearer and the width direction that is orthogonal to the longitudinal direction, wherein:
 the projecting-and-depressed sheet has the plurality of depressions and projections on the skin-facing surface to be brought into contact with the wearer's skin;
 in the given direction, the movable range of the apex of the projection of the projecting-and-depressed sheet is from 35 to 100% to the length of the bottom portion of the projection;
 on the skin-facing surface of the projecting-and-depressed sheet, the mean friction coefficient MIU in the given direction is from 0.1 to 0.27, and the difference in friction coefficient between the forward path and the return path when moved back and forth along the given direction is from 0.001 to 0.07; and
 the work of compression of the projecting-and-depressed sheet is from 2.5 to 20 mN·cm/cm' and the compression recovery rate is from 46 to 85%.

{18}
The absorbent article as set forth in clause {1}, the absorbent article comprising the projecting-and-depressed sheet as a constituent member and having the longitudinal direction that corresponds to the front-rear direction of the wearer and the width direction that is orthogonal to the longitudinal direction, wherein:
 the projecting-and-depressed sheet has the plurality of depressions and projections on the skin-facing surface to be brought into contact with the wearer's skin;

in the given direction, the movable range of the apex of the projection of the projecting-and-depressed sheet is from 45 to 85% to the length of the bottom portion of the projection;

on the skin-facing surface of the projecting-and-depressed sheet, the mean friction coefficient MIU in the given direction is from 0.1 to 0.24, and the difference in friction coefficient between the forward path and the return path when moved back and forth along the given direction is from 0.001 to 0.04; and the work of compression of the projecting-and-depressed sheet is from 3.5 to 20 mN·cm/cm' and the compression recovery rate is from 52 to 85%.

{19}

The absorbent article as set forth in any one of clauses {1} to {18}, wherein:

the projecting-and-depressed sheet is a composite sheet including a first sheet and a second sheet that are layered on one another and that are joined together at a plurality of joined portions;

the first sheet forms the projections that project in a direction separating from the second sheet at sections other than the joined portions;

the projection's outer peripheral length, in the given direction, along the projection's surface within a cross section in a thickness direction of the projecting-and-depressed sheet is at least 1.2 times the length, in the given direction, of the bottom portion of the projection; and a length between respective apexes of the projections adjacent to one another in the given direction is from 0.5 to 5 times a depth of the depression located between those projections.

{20}

The absorbent article as set forth in any one of clauses {1} to {18}, wherein:

the projecting-and-depressed sheet is a composite sheet including a first sheet and a second sheet that are layered on one another and that are joined together at a plurality of joined portions;

the first sheet forms the projections that project in a direction separating from the second sheet at sections other than the joined portions;

the projection's outer peripheral length, in the given direction, along the projection's surface within a cross section in a thickness direction of the projecting-and-depressed sheet is from 1.2 to 3 times the length, in the given direction, of the bottom portion of the projection; and a length between respective apexes of the projections adjacent to one another in the given direction is from 0.5 to 5 times a depth of the depression located between those projections.

{21}

The absorbent article as set forth in any one of clauses {1} to {18}, wherein:

the projecting-and-depressed sheet is a composite sheet including a first sheet and a second sheet that are layered on one another and that are joined together at a plurality of joined portions;

the first sheet forms the projections that project in a direction separating from the second sheet at sections other than the joined portions;

the projection's outer peripheral length, in the given direction, along the projection's surface within a cross section in a thickness direction of the projecting-and-depressed sheet is from 1.3 to 2.5 times the length, in the given direction, of the bottom portion of the projection; and a length between respective apexes of the projections adjacent to one another in the given direction is from 1 to 4 times a depth of the depression located between those projections.

{22}

The absorbent article as set forth in any one of clauses {1} to {18}, wherein:

the projecting-and-depressed sheet is a composite sheet including a first sheet and a second sheet that are layered on one another and that are joined together at a plurality of joined portions;

the first sheet forms the projections that project in a direction separating from the second sheet at sections other than the joined portions;

the projection's outer peripheral length, in the given direction, along the projection's surface within a cross section in a thickness direction of the projecting-and-depressed sheet is from 1.4 to 2 times the length, in the given direction, of the bottom portion of the projection; and a length between respective apexes of the projections adjacent to one another in the given direction is from 1.5 to 3 times a depth of the depression located between those projections.

{23}

The absorbent article as set forth in clause {17}, wherein:

the projecting-and-depressed sheet is a composite sheet including a first sheet and a second sheet that are layered on one another and that are joined together at a plurality of joined portions;

the first sheet forms the projections that project in a direction separating from the second sheet at sections other than the joined portions;

the projection's outer peripheral length, in the given direction, along the projection's surface within a cross section in a thickness direction of the projecting-and-depressed sheet is from 1.3 to 2.5 times the length, in the given direction, of the bottom portion of the projection; and a length between respective apexes of the projections adjacent to one another in the given direction is from 1 to 4 times a depth of the depression located between those projections.

{24}

The absorbent article as set forth in clause {18}, wherein:

the projecting-and-depressed sheet is a composite sheet including a first sheet and a second sheet that are layered on one another and that are joined together at a plurality of joined portions;

the first sheet forms the projections that project in a direction separating from the second sheet at sections other than the joined portions:

the projection's outer peripheral length, in the given direction, along the projection's surface within a cross section in a thickness direction of the projecting-and-depressed sheet is from 1.4 to 2 times the length, in the given direction, of the bottom portion of the projection; and a length between respective apexes of the projections adjacent to one another in the given direction is from 1.5 to 3 times a depth of the depression located between those projections.

{25}

The absorbent article as set forth in any one of clauses {19} to {22}, wherein:
the first sheet includes a first layer on the skin-facing surface side and a second layer on a non-skin-facing surface side; and
the second layer includes first fibers and second fibers satisfying at least one of the following conditions (1) to (4), the second layer including a larger amount of the second fibers than the first layer, a content of the second fibers in the second layer being at least 2 times a content of the second fibers in the first layer:
(1) a melting point of a constituent component of the second fibers is higher than that of a constituent component of the first fibers;
(2) a fiber diameter of the second fibers is greater than that of the first fibers;
(3) the second fibers are crimped fibers having a greater number of crimps than the first fibers; and
(4) the first fibers and the second fibers are core-sheath conjugate fibers, wherein a diameter ratio of a sheath component in the core-sheath conjugate fiber constituting the second fibers is lower than that of the first fibers.

{26}

The absorbent article as set forth in any one of clauses {1} to {25}, wherein the projecting-and-depressed sheet has a cool contact sensation q-max of 0.7 kW/m² or less.

{27}

The absorbent article as set forth in any one of clauses {1} to {25}, wherein the projecting-and-depressed sheet has a cool contact sensation q-max of from 0.2 to 0.7 kW/m².

{28}

The absorbent article as set forth in any one of clauses {1} to {25}, wherein the projecting-and-depressed sheet has a cool contact sensation q-max of from 0.2 to 0.6 kW/m².

{29}

The absorbent article as set forth in any one of clauses {1} to {25}, wherein the projecting-and-depressed sheet has a cool contact sensation q-max of from 0.2 to 0.5 kW/m².

{30}

The absorbent article as set forth in clause {17}, wherein the projecting-and-depressed sheet has a cool contact sensation q-max of from 0.2 to 0.6 kW/m².

{31}

The absorbent article as set forth in clause {18}, wherein the projecting-and-depressed sheet has a cool contact sensation q-max of from 0.2 to 0.5 kW/m².

{32}

The absorbent article as set forth in any one of clauses {1} to {31}, wherein:
the absorbent article includes a widthwise elasticized region capable of stretching and contracting along the width direction; and
the projecting-and-depressed sheet partially overlaps the widthwise elasticized region.

{33}

The absorbent article as set forth in any one of clauses {1} to {32}, wherein:
the absorbent article comprises a topsheet constituted by the projecting-and-depressed sheet, a backsheet, and an absorbent member arranged between the topsheet and the backsheet;
the absorbent article includes, in the longitudinal direction,
a front portion to be arranged on the wearer's front side when the absorbent article is worn,
a rear portion to be arranged on the wearer's rear side when the absorbent article is worn, and
a crotch portion located between the front portion and the rear portion; and
the movable range, in the longitudinal direction, of the apex of the projection is longer in the projecting-and-depressed sheet in the rear portion than in the crotch portion.

{34}

The absorbent article as set forth in any one of clauses {1} to {33}, wherein:
the projecting-and-depressed sheet has a function of increasing an amount of oxytocin in a biological sample by bringing the projecting-and-depressed sheet into contact with the skin or hair and applying tactile stimulation; and
the amount of oxytocin is measured by a method including steps (A) to (C) below:
(A) a step of bringing a test sheet to be evaluated into contact with the skin or hair of an animal and applying tactile stimulation to the animal;
(B) a step of sampling a biological sample from the animal after applying the tactile stimulation; and
(C) a step of measuring the amount of oxytocin in the biological sample.

{35}

The absorbent article as set forth in clause {34}, wherein, in the step (B), the biological sample is sampled from the animal within 60 minutes after applying the tactile stimulation.

EXAMPLES

The present invention is described in further detail below according to examples thereof. The present invention, however, is not limited to the following examples.

Working Example 1

A projecting-and-depressed sheet including depressions and projections formed according to the pattern illustrated in FIG. 3 was prepared. The projecting-and-depressed sheet was prepared according to the aforementioned method; that is, a first sheet deformed into a projecting-and-depressed shape was superposed on a second sheet, and the two sheets were joined together by fusion-bonding. At this time, the intermeshing depth between the first and second rollers was adjusted so that the ratio L7/L2 was 1.5, L7 being the projection's outer peripheral length within the thickness-direction cross section along the projecting-and-depressed sheet's longitudinal direction, and L2 being the length of the bottom portion of the projection in the same direction. The depressions were formed in sections other than the projections. For the first sheet, a sheet including a first layer and a second layer was used. For the sheet constituting each of the first and second layers, a nonwoven fabric made by the air-through method and having a basis weight of 18 g/m² was used. The nonwoven fabric constituting the first layer was made of first fibers. The nonwoven fabric constituting the second layer was made of first fibers and second fibers, wherein the mass ratio of the first fibers to the second fibers in the second layer was 70/30 (first fibers/second fibers). For the first fibers and the second fibers, fibers having a core-sheath structure, wherein the core component was polyethylene terephthalate (PET) and the sheath component was polyethylene (PE), were used. The first fibers had a diameter ratio between the core component and the sheath component of 1.57 (core component/sheath component). The second fibers had a diameter ratio between the core component and the sheath component of 1.17 (core component/sheath component). For the second sheet, a sheet identical to the nonwoven fabric constituting the first layer was used.

Working Example 2

A projecting-and-depressed sheet was prepared according to the same method as in Working Example 1, except that the intermeshing depth between the first and second rollers was adjusted such that the ratio L7/L2 was 1.2, and depressions and projections were formed according to the pattern illustrated in FIG. 12.

Working Example 3

A sheet was prepared according to the same method as in Working Example 1, except that the intermeshing depth was reduced such that the ratio L7/L2 was 1.3.

Comparative Example 1

A sheet was prepared according to the same method as in Working Example 2, except that the intermeshing depth was reduced such that the ratio L7/L2 was 1.1.

Comparative Example 2

A sheet was prepared according to the same method as in Working Example 1, except that the first sheet was not deformed into a projecting-and-depressed shape.

Comparative Example 3

A fabric, Nemu Animals (registered trademark) from Liv Heart Corporation, used for stuffed toys was prepared as the sheet. The constituent fibers of the stuffed toy fabric included 95 mass % polyester and 5 mass % polyurethane.

For each of the sheets of Working Examples 1 to 3 and Comparative Examples 1 to 3, the movable range of the apex of the projections, the surface properties of the sheet's skin-facing surface, the sheet's physical properties, and the dimensions related to the projection are shown in Table 1 below. These are measured according to the aforementioned measurement methods. Herein, the sheet's skin-facing surface is the surface that contacts the panelist's hand in the measurement of the amount of oxytocin described below. The movable range of the apex in the sheet's longitudinal direction was measured as the movable range of the apex of the projections. The mean friction coefficient MIU in the sheet's longitudinal direction and the difference in friction coefficient between the forward path and the return path were also measured.

{Measurement of Amount of Oxytocin}

Diapers in a spread-open state as illustrated in FIG. 1 were prepared by using the respective sheets of Working Examples 1 to 3 and Comparative Examples 1 to 3 as each diaper's topsheet. Each sheet was incorporated into the respective diaper such that the sheet's longitudinal direction matched the diaper's longitudinal direction. Each sheet including projections was incorporated into the respective diaper such that the surface having the projections constituted the skin-facing surface. Each diaper was placed so that the surface of the topsheet faced upward. Ten healthy female panelists in their twenties or thirties were asked to touch each diaper's topsheet to apply tactile stimulation. Each panelist's saliva was sampled as a biological sample before and after application of the tactile stimulation. Tactile stimulation was applied to each panelist by making the palms of both hands touch the diaper's topsheet. To apply tactile stimulation, a cycle including a step of moving the palms back and forth along the diaper's longitudinal direction for 30 seconds in a state where the palms are in contact with the diaper's topsheet, and a step of resting the palms so as not to contact anything for 30 seconds, was repeated five times. After 30 minutes from applying tactile stimulation, each panelist was asked to rinse the oral cavity with water and then discharge all the saliva within the oral cavity into a centrifugation tube over 10 minutes, to thereby obtain a biological sample. Also, according to the same method, saliva was sampled over 10 minutes at a timing 30 minutes before application of the tactile stimulation, as a biological sample before tactile stimulation. The sampled saliva was immediately cooled with dry ice and stored at −80° C.

The sampled saliva was subjected to centrifugal separation at 15,000 rpm for 10 minutes. The supernatant was sampled, and mixed with an equal volume of 0.1% (v/v) trifluoroacetic acid (TFA). The mixture was subjected to centrifugal separation at 3,000 rpm for 30 minutes. The supernatant was sampled, and subjected to the following extraction using a Sep-Pak C18 column (200 mg, 3 cc from Waters Corporation). First, 1 mL of 100% acetonitrile (ACN) was passed through the C18 column, followed by 10 mL of 0.1% (v/v) TFA solution. Then, the column was applied with the entire amount (3.0-6.0 mL) of the saliva mixed with the 0.1% (v/v) TFA solution, and washed with 10 mL of 0.1% (v/v) TFA solution. The sample was then eluted by applying 3 mL of a solution including 95% of ACN and 5% of 0.1% (v/v) TFA solution. ACN in the eluted solution was evaporated under $N_2$ gas, and the remaining aqueous solution was lyophilized. The lyophilizate was dissolved in 250 μL of Assay Buffer of an Oxytocin ELISA kit (from Enzo). The amount of oxytocin in the saliva was determined with this kit.

In Table 1 below, the change in the amount of oxytocin before and after tactile stimulation was evaluated according to the following criteria.

+++: The amount of oxytocin after tactile stimulation increased by at least 50% compared to the amount of oxytocin before tactile stimulation.

++: The amount of oxytocin after tactile stimulation increased by at least 30% to less than 50% compared to the amount of oxytocin before tactile stimulation.

+: The amount of oxytocin after tactile stimulation increased by at least 10% to less than 30% compared to the amount of oxytocin before tactile stimulation.

+−: The amount of oxytocin after tactile stimulation increased/decreased by less than 10% compared to the amount of oxytocin before tactile stimulation.

−: The amount of oxytocin after tactile stimulation decreased by at least 10% to less than 30% compared to the amount of oxytocin before tactile stimulation −−: The amount of oxytocin after tactile stimulation decreased by at least 30% to less than 50% compared to the amount of oxytocin before tactile stimulation.

−−−: The amount of oxytocin after tactile stimulation decreased by at least 50% compared to the amount of oxytocin before tactile stimulation.

{Evaluation of Texture}

Diapers in a spread-open state as illustrated in FIG. 1 were prepared by using the respective sheets of Working Examples 1 to 3 and Comparative Examples 1 to 3 as the topsheet. According to the same method as in the aforementioned {Measurement of Amount of Oxytocin}, ten healthy female panelists in their twenties or thirties were asked to touch each diaper's topsheet which was placed in a box, and evaluate the texture of each topsheet. More specifically, "comfortableness" when moving the palm back and forth five times along the diaper's longitudinal direction in a state where the palm was in contact with the topsheet was evaluated according to the following 7-point scale, to find the average value.
  3: The sheet feels very good.
  2: The sheet feels good.
  1: The sheet feels rather good.
  0: Cannot say whether the sheet feels good or bad.
  −1: The sheet feels rather bad.
  −2: The sheet feels bad.
  −3: The sheet feels very bad.

In the above evaluation of texture, an average value of 2.5 or higher was rated "+++", from 1.5 to lower than 2.5 was rated "++", from 0.5 to lower than 1.5 was rated "+", from −0.5 to lower than 0.5 was rated "+−", from −1.5 to lower than −0.5 was rated "−", from −2.5 to lower than −1.5 was rated "−−", and an average value of lower than −2.5 was rated "−−−", which are shown as evaluation results in Table 1.

TABLE 1

| | Working Example 1 | Working Example 2 | Working Example 3 | Comparative Example 1 | Comparative Example 2 | Comparative Example 3 |
|---|---|---|---|---|---|---|
| Movable range of apex of projections (%) | 48 | 43 | 40 | 29 | — | — |
| Surface properties of skin-facing surface — Friction coefficient MIU | 0.22 | 0.26 | 0.25 | 0.26 | 0.16 | 0.32 |
| Surface properties of skin-facing surface — Difference in friction coefficient between forward and return paths | 0.03 | 0.03 | 0.03 | 0.00 | 0.04 | 0.46 |
| Compression properties — Work of compression (mN·cm/cm$^2$) | 4.1 | 4.4 | 2.2 | 2.0 | 0.5 | 2.1 |
| Compression properties — Compression recovery rate (%) | 73.2 | 68.1 | 46.2 | 45.0 | 48.4 | 32.7 |
| Projection's outer peripheral length/bottom portion's length (L7/L2) | 1.5 | 1.2 | 1.3 | 1.1 | — | — |
| Distance between apexes of adjacent projections/depression's depth (L4/D) | 2.9 | 3.2 | 3.8 | 4.0 | — | — |
| Cool contact sensation q-max (kW/m$^2$) | 0.48 | 0.57 | 0.51 | 0.62 | 1.23 | 0.88 |
| Change in amount of oxytocin | +++ | ++ | + | +− | +− | − |
| Evaluation of texture | +++ | ++ | + | +− | − | − |

The results of Table 1 show that Working Examples 1 to 3 exhibited an increase in the amount of oxytocin by tactile stimulation from the diaper's topsheet. This verifies that tactile stimulation from the diaper's topsheet has an effect of producing a pleasant sensation. The results of Working Examples 1 to 3 also show that, the higher the rating of the texture, the further the amount of oxytocin increases. In contrast, the sheets of Comparative Examples 1 to 3 did not exhibit an increase in the amount of oxytocin by tactile stimulation, and the rating of texture was also poor.

INDUSTRIAL APPLICABILITY

The present invention can provide an absorbent article capable of easily offering a pleasant sensation to a user, such as a wearer, when the user touches a sheet.

The invention claimed is:

1. An absorbent article comprising a projecting-and-depressed sheet as a constituent member, the absorbent article having a longitudinal direction that corresponds to a front-rear direction of a wearer and a width direction that is orthogonal to the longitudinal direction, wherein:
  the projecting-and-depressed sheet has a plurality of depressions and projections on a skin-facing surface to be brought into contact with the wearer's skin;
  in a given direction, a movable range of an apex of the projection of the projecting-and-depressed sheet is 30% or greater to a length of a bottom portion of the projection;
  on the skin-facing surface of the projecting-and-depressed sheet, a mean friction coefficient MIU in the given direction is 0.3 or less, and a difference in friction coefficient between a forward path and a return path when moved back and forth along the given direction is less than 0.1;
  the projecting-and-depressed sheet has a work of compression of 2.0 mN·cm/cm$^2$ or greater and a compression recovery rate of 40% or greater;
  the projecting-and-depressed sheet is a composite sheet including a first sheet and a second sheet that are layered on one another and that are joined together at a plurality of joined portions;
  the first sheet forms the projections that project in a direction separating from the second sheet at sections other than the joined portions;
  the projection's outer peripheral length, in the given direction, along the projection's surface within a cross section in a thickness direction of the projecting-and-depressed sheet is at least 1.2 times the length, in the given direction, of the bottom portion of the projection; and
  a length between respective apexes of the projections adjacent to one another in the given direction is from 0.5 to 5 times a depth of the depression located between those projections;
  the first sheet includes a first layer on the skin-facing surface side and a second layer on a non-skin-facing surface side; and
  the first layer and the second layer include first fibers and second fibers satisfying the following condition (3) or the following conditions (2) to (3), the second layer including a larger amount of the second fibers than the first layer, a content of the second fibers in the second layer being at least 2 times a content of the second fibers in the first layer:
  (2) a fiber diameter of the second fibers is greater than that of the first fibers; and
  (3) the second fibers are crimped fibers having a greater number of crimps than the first fibers.

2. The absorbent article according to claim 1, wherein the movable range of the apex of the projection is from 30 to 100% to the length of the bottom portion of the projection.

3. The absorbent article according to claim 1, wherein the mean friction coefficient MIU is from 0.1 to 0.3.

4. The absorbent article according to claim 1, wherein the difference in friction coefficient is 0.001 or greater to less than 0.1.

5. The absorbent article according to claim 1, wherein the work of compression is from 2.0 to 20 mN·cm/cm$^2$.

6. The absorbent article according to claim 1, wherein the compression recovery rate is from 40 to 85%.

7. The absorbent article according to claim 1, the absorbent article comprising the projecting-and-depressed sheet as a constituent member and having the longitudinal direction that corresponds to the front-rear direction of the wearer and the width direction that is orthogonal to the longitudinal direction, wherein:
the projecting-and-depressed sheet has the plurality of depressions and projections on the skin-facing surface to be brought into contact with the wearer's skin;
in the given direction, the movable range of the apex of the projection of the projecting-and-depressed sheet is from 35 to 100% to the length of the bottom portion of the projection;
on the skin-facing surface of the projecting-and-depressed sheet, the mean friction coefficient MIU in the given direction is from 0.1 to 0.27, and the difference in friction coefficient between the forward path and the return path when moved back and forth along the given direction is from 0.001 to 0.07; and
the work of compression of the projecting-and-depressed sheet is from 2.5 to 20 mN·cm/cm$^2$ and the compression recovery rate is from 46 to 85%.

8. The absorbent article according to claim 1, wherein the projecting-and-depressed sheet has a cool contact sensation q-max of 0.7 kW/m$^2$ or less.

9. The absorbent article according to claim 1, wherein the projecting-and-depressed sheet has a cool contact sensation q-max of from 0.2 to 0.6 kW/m$^2$.

10. The absorbent article according to claim 1, wherein the projecting-and-depressed sheet has a cool contact sensation q-max of from 0.2 to 0.5 kW/m$^2$.

11. The absorbent article according to claim 1, wherein:
the absorbent article includes a widthwise elasticized region capable of stretching and contracting along the width direction; and
the projecting-and-depressed sheet partially overlaps the widthwise elasticized region.

12. The absorbent article according to claim 1, wherein:
the absorbent article comprises a topsheet constituted by the projecting-and-depressed sheet, a backsheet, and an absorbent member arranged between the topsheet and the backsheet;
the absorbent article includes, in the longitudinal direction,
a front portion to be arranged on the wearer's front side when the absorbent article is worn,
a rear portion to be arranged on the wearer's rear side when the absorbent article is worn, and
a crotch portion located between the front portion and the rear portion; and
the movable range, in the longitudinal direction, of the apex of the projection is longer in the projecting-and-depressed sheet in the rear portion than in the crotch portion.

13. The absorbent article according to claim 1, wherein:
the projecting-and-depressed sheet has a function of increasing an amount of oxytocin in a biological sample by bringing the projecting-and-depressed sheet into contact with the skin or hair and applying tactile stimulation; and
the amount of oxytocin is measured by a method including steps (A) to (C) below:
(A) a step of bringing a test sheet to be evaluated into contact with the skin or hair of an animal and applying tactile stimulation to the animal;
(B) a step of sampling a biological sample from the animal after applying the tactile stimulation; and
(C) a step of measuring the amount of oxytocin in the biological sample.

14. An absorbent article comprising a projecting-and-depressed sheet as a constituent member, the absorbent article having a longitudinal direction that corresponds to a front-rear direction of a wearer and a width direction that is orthogonal to the longitudinal direction, wherein:
the projecting-and-depressed sheet has a plurality of depressions and projections on a skin-facing surface to be brought into contact with the wearer's skin;
in a given direction, a movable range of an apex of the projection of the projecting-and-depressed sheet is 30% or greater to a length of a bottom portion of the projection;
on the skin-facing surface of the projecting-and-depressed sheet, a mean friction coefficient MIU in the given direction is 0.3 or less, and a difference in friction coefficient between a forward path and a return path when moved back and forth along the given direction is less than 0.1;
the projecting-and-depressed sheet has a work of compression of 2.0 mN·cm/cm$^2$ or greater and a compression recovery rate of 40% or greater;
the projecting-and-depressed sheet is a composite sheet including a first sheet and a second sheet that are layered on one another and that are joined together at a plurality of joined portions, wherein the joined portions are flat;
the first sheet forms the projections that project in a direction separating from the second sheet at sections other than the joined portions;
the projection's outer peripheral length, in the given direction, along the projection's surface within a cross section in a thickness direction of the projecting-and-depressed sheet is at least 1.2 times the length, in the given direction, of the bottom portion of the projection; and
a length between respective apexes of the projections adjacent to one another in the given direction is from 0.5 to 5 times a depth of the depression located between those projections;
the first sheet includes a first layer on the skin-facing surface side and a second layer on a non-skin-facing surface side; and
the first layer and the second layer include first fibers and second fibers satisfying the following condition (3) or the following conditions (2) to (3), the second layer including a larger amount of the second fibers than the first layer, a content of the second fibers in the second layer being at least 2 times a content of the second fibers in the first layer:

(2) a fiber diameter of the second fibers is greater than that of the first fibers; and
(3) the second fibers are crimped fibers having a greater number of crimps than the first fibers.

* * * * *